(12) United States Patent
Chomet et al.

(10) Patent No.: US 6,331,660 B1
(45) Date of Patent: Dec. 18, 2001

(54) MAIZE DIMBOA BIOSYNTHESIS GENES

(75) Inventors: Paul S. Chomet, Mystic, CT (US); Monika Frey, Garching; Alfons Gierl, Munich, both of (DE)

(73) Assignee: Dekalb Genetics Corporation, Dekalb, IL (US)

( * ) Notice: Subject to any disclaimer, the term of this patent is extended or adjusted under 35 U.S.C. 154(b) by 0 days.

(21) Appl. No.: 09/039,046

(22) Filed: Mar. 13, 1998

Related U.S. Application Data

(60) Provisional application No. 60/040,513, filed on Mar. 13, 1997.

(51) Int. Cl.⁷ .............................. A01H 1/00; A01H 4/00; A01H 25/00; A01H 5/10; C12N 15/29
(52) U.S. Cl. ..................... 800/278; 800/279; 800/283; 800/284; 800/289; 800/290; 800/295; 800/298; 800/300; 800/300.1; 800/301; 800/302; 800/312; 800/314; 800/317; 800/317.2; 800/317.3; 800/320; 800/320.1; 435/69.1; 435/440; 435/419; 435/418; 536/320.1; 536/23.1; 536/236
(58) Field of Search ................................. 536/23.6, 320.1, 536/23.1; 800/278, 279, 283, 284, 289, 290, 295, 298, 300, 300.1, 301, 302, 312, 314, 317, 317.2, 317.3, 32, 320.1; 435/69.1, 440, 410, 419, 418

(56) References Cited

U.S. PATENT DOCUMENTS

| 5,538,880 | 7/1996 | Lundquist et al. .................... 800/265 |
| 5,550,318 | 8/1996 | Adams et al. ...................... 800/300.1 |

FOREIGN PATENT DOCUMENTS

| WO 93/22441 | 11/1993 | (WO) . |
| WO93/22441 * | 11/1993 | (WO) . |
| WO 95/06128 | 3/1995 | (WO) . |
| WO 96/16041 | 6/1995 | (WO) . |
| WO 98/40504 | 9/1998 | (WO) . |

OTHER PUBLICATIONS

Napoli et al. 1989. vol. 2: 278–289.*
Carvalho et al. EMBO J. 1992. vol. 11:2595–2602.*
Linthorst et al. Plant Cell. 1989. Mar. 1:285–291.*
Frey et al. Science. 1997. Aug. 1 issue. vol. 277:696–699.*
Kramer et al. Plant Molecular Biology. 1995. Mar. vol. 27:1183–1188.*
Gordon–Kamm et al. The Plant Cell. 1990. vol. 2:603–618.*
Åhman and Johansson, "Effect of light on DIMBOA–glucoside concentration in wheat (*Triticum aestivum* L.)," *Ann. Appl. Biol.*, 124:569–574, 1994.
Bailey and Larson, "Hydroxamic acid glucosyltransferases from maize seedlings," *Plant Physiol.*, 90:1071–1076, 1989.
Bailey and Larson, "Maize microsomal benzoxazinone N–Monooxygenase," *Plant Physiol.*, 95:792–796, 1991.

Burr and Burr, "Recombinant inbreds for molecular mapping in maize: theoretical and practical considerations," *Trends Genet.*, 7(2):55–60, 1991.

Campos et al., "Toxicokinetics of 2,4–dihydroxy–7–methoxy–1,4–benzoxazin–3–one (Dimboa) in the European Corn Borer," *J. Chem. Ecol.*, 15(7):1989.

Chomet, "Transposon tagging with mutator," Freeling and Walbot, Eds., In: *The Maize Handbook*, Springer–Verlag, New York, 27:243–249, 1994.

Couture et al., "Resistance of maize to *H. turcicum*," *Physiol. Plant Pathol.*, 1:515–521, 1971.

Cuevas et al., "Reaction of dimboa, a resistance factor from cereals, with α–chymotrypsin," *Phytochemistry*, 29(5),1429–1432, 1990.

Desai, "Indole is an intermediate in the biosynthesis of cyclic hydroxami acids in maize," *Chem. Commun.*, 1321, 1996.

Dunn et al., "Inheritance of cyclic hydroxamates in *Zea mays* L.," *Can. J. Plant Sci.*, 61:583, 1981.

Frey et al., "Analysis of a chemical plant defense mechanism in grasses," *Science*, 277(5326):696–699, 1997.

Frey et al., "Expression of a cytochrome P450 gene family in maize," *Mol Gen. Genet.*, 246:100–109, 1995.

Frey et al., "Z. mays CYP71C1 mRNA for cytochrome P–450," EMBL Sequence Database, Accession No. X81827, Sep. 26, 1994.

Frey et al., "Z. mays CYP71C1 mRNA for cytochrome P–450," EMBL Sequence Database, Accession No. X81828, Sep. 26, 1994.

Frey et al., "Z. mays CYP71C2 mRNA for cytochrome P–450," EMBL Sequence Database, Accession No. X81829, Sep. 26, 1994.

Frey et al., "Z. mays CYP71C3 mRNA for cytochrome P–450," EMBL Sequence Database, Accession No. X81830, Sep. 26, 1994.

Frey et al., "Z. mays CYP71C4 mRNA for cytochrome P–450," EMBL Sequence Database, Accession No. X81831, Sep. 26, 1994.

(List continued on next page.)

*Primary Examiner*—Amy J. Nelson
*Assistant Examiner*—O. M. F. Zaghmout
(74) *Attorney, Agent, or Firm*—Fulbright & Jaworski LLP

(57) ABSTRACT

The identification of the maize Bx1 gene involved in benzoxazinone biosynthesis activity is described. This Bx1 gene, as well as other benzoxazinone biosynthesis genes, provide valuable tools for the production of plants with enhanced expression profiles of bezoxazinone synthesis, and therefore, resistance to insect infestation.

60 Claims, 7 Drawing Sheets

OTHER PUBLICATIONS

Gierl et al., "Z. mays CYP71C4 gene," EMBL Databank Accession No. Y11368, Feb. 24, 1997.
Gierl et al., "Z. mays CYP71C3 gene," EMBL Databank Accession No. Y11403, Mar. 3, 1997.
Gierl et al., "Z. mays CYP71C2 gene," EMBL Databank Accession No. Y11404, Mar. 3, 1997.
Gierl et al., "Genetic analysis of the dimboa biosynthetic pathway of Zea mays," Database BIOSIS Biosciences Information Service, Philadelphia, PA, USA, DN 99537555, *International Conference on Perspectives in Plant Genetics*, Warsaw, Poland, Sep. 16–17, 1996. *Journal of Applied Genetics*, 37A(0):50–51, 1996.
Guthrie and Barry, "Evaluation of a mutable system for inducing resistance to European corn borer (Lepidoptera: Pyralidae) in susceptible inbred lines of dent maize," *J. Kansas Entomol. Soc.*, 56(4):552–554, 1983.
Hamilton, "A corn mutant deficient in 2.4–Dihydroxy–7–methoxy–1,4–benzoxazin–3–one with an altered tolerance of atrazine," *Weeds*, 12:27–30, 1964.
Hamilton, "Tolerance of several grass species to 2–chloro–s–triazine herbicides in relation to degradation and content of benzoxazinone derivatives," *Agri. Food Chem.*, 12(1):14–17, 1964.
Hyde et al., "Three–dimensional structure of the tryptophan synthase $\alpha_2\beta_2$ multienzyme complex from *Salmonella typhimurium*," *J. Biol. Chem.*, 263(33):17857–17871, 1988.
International Search Report dated Jul. 29, 1998 (PCT/US98/05078) (DEKM:131P).
Klun and Robinson, "Concentration of two, 1–4–benzoxazinones in dent corn at various stages of development of the plant and its relation to resistance of the host plant to the European corn borer," *J. Econ. Entomol.*, 62(1):214–220, 1969.
Klun et al., "Genetic nature of the concentration of 2,4–dihydroxy–7–methoxy 2H–1,4–benzoxazin–3(4H)–one and resistance to the European corn borer in a diallel set of eleven maize inbreds," *Crop Sci.*, 10:87–90, 1970.
Klun et al., "2,4–dihydroxy–7–methoxy–1,4–benzoxazin–3–one (DIMBOA), an active agent in the resistance of maize to the European Corn Borer," *J. Econ. Entomol.*, 60:1529–1533, 1967.
Konieczny and Ausubel, "A procedure for mapping *Arabidopsis* mutations using co–dominant ecotype–specific PCR––based markers," *Plant J.*, 4(2):403–410, 1993.
Kramer and Koziel, "Structure of a maize tryptophan synthase alpha subunit gene with pith enhanced expression," *Plant Mol. Biol.*, 27:1183–1188, 1995.
Kramer et al., "Z. mays (C6000237) trpA gene," EMBL Sequence Database, Accession No. X76713, Jan. 10, 1994.
Kutchan, "Alkaloid biosynthesis — the basis for metabolic engineering of medicinal plants," *Plant Cell*, 7:1059–1070, 1995.
Last and Fink, "Tryptophan–requiring mutants of the plant *Arabidopsis thaliana*," *Science*, 240:305–310, 1988.
Last et al., "Tryptophan mutants in *Arabidopsis*: the consequences of duplicated tryptophan synthase $\beta$ genes," *Plant Cell*, 3:345–358, 1991.
Long et al., "Relationship of hydroxamic acid content in corn and resistance to northern corn leaf Aphid," *Crop Sci.*, 17:55–58, 1977.
Long et al., "Relationship of hydroxamic acid content in maize and resistance to northern corn leaf blight," *Crop Sci.*, 15:333–335, 1975.
Long et al., "Relation of hydoxamic acid concentration (DIMBOA) to resistance to the corn leaf aphid," *Maize Genetics Newsletter*, p. 91, 1976.
Long et al., "Relation of hydroxamic concentration to resistance to *Helminthosporium turcicum* in the field," *Maize Genetics Newsletter*, p. 71, 1977.
Long et al., "Two cycles of recurrent selection for hydroxamate concentration," *Maize Genetics Newsletter*, pp. 70–71, 1977.
Long et al., "Rapid procedure for estimating cyclic hydroxamate (DIMBOA) concentration in maize," *Crop Sci.*, 14:601–603, 1974.
Neuffer and Chang, "Duplicate factors for orange pericarp (orp)," Source unknown.
Newhouse et al., "Mutations in corn (Zea mays L.) conferring resistance to imidazolinone herbicides," *Theor. Appl. Genet.*, 83:65–70, 1991.
Niederberger et al., "A strategy for increasing an in vivo flux by genetic manipulations," *Biochem. J.*, 286:1–7, 1992.
Niemeyer, "Hydroxamic acids (4–hydroxy–1, 4–benzoxazin–3–ones), defence chemicals in the gramineae," *Photochem.*, 27:3349–3358, 1988.
Niyogi and Fink, "Two anthranilate synthase genes in Arabiodopsis: defense–related regulation of the tryptophan pathway," *Plant Cell*, 4:721–733, 1992.
Peng and Chilton, "Biosynthesis of DIMBOA in maize using deuterium oxide as a tracer," *Phytochem.*, 37(1):167–171, 1994.
Radwanski et al., "*Arabidopsis thaliana* tryptophan synthase alpha: gene cloning, expression, and subunit interaction," *Mol. Gen. Genet.*, 248(6):657–667, 1995.
Robinson et al., "European corn borer: a nonpreference mechanism of leaf feeding resistance and its relationship to 1,4–benzoxazin–3–one concentration in dent corn tissue," *J. Econ. Entomol.*, 71(3):461–465, 1978.
Robinson et al., Éuropean corn borer (Lepidoptera: Pyralidae) leaf feeding resistance: Dimboa Bioassays, *J. Kansas Entomol. Soc.*, 55(2):357–364, 1982.
Sahi et al., "Corn metabolites affect growth and virulence of *Agrobacterium tumefaciens*," *Proc. Natl. Acad. Sci. USA*, 87:3879–3883, 1990.
Simcox and Weber, "Location of the benzoxazinless (bx) locus in maize by monosomic and B–A translocational analyses," *Crop. Sci.*, 25:827–830, 1985.
Stuber et al., "Genetic control and racial variation of $\beta$–Glucosidase isozymes in maize (Zea mays L.)," *Biochem. Genet.*, 15:383–394, 1977.
Sullivan et al., "Resistance of exotic maize varieties to the European Corn Borer *Ostrinia* nubilalis (Hübner)," *Env. Ent.*, 3(4):718–720, 1974.
Tipton and Buell, "Ferric iron complexes of hydroxamic acids from maize," *Phytochem.*, 9:1215–1217, 1970.
Tipton et al., "Catalysis of simazine hydrolysis by 2,4–dihydroxy–7–methoxy–1,4–benzoxazin–3–one," *Agri. Food Chem.*, 19(3):484–486, 1971.
Wahlroos and Virtanen, "The precursors of 6–methoxybenzoxazolinone in maize and wheat plants, their isolation and some of their properties," *Acta Chem. Scand.*, 13:1906–1908, 1959.
Weischet and Kirschner, "The mechanism of the synthesis of indoleglycerol phosphate catalyzed by tryptophan synthase from *Escherichia coli*. Steady–state kinetic studies," *Eur. J. Biochem.*, 65(2):365–373, 1976.

Widholm, "Utilization of indole analogs by carrot and tobacco cell tryptophan synthase in vivo and in vitro," *Plant Physiol.*, 67:1101–1104, 1981.

Woodward et al., "Decomposition of 2,4-dihydroxy-7-methoxy-2H-1,4-benzoxazin-3(4H)-one in aqueous solutions," *Plant Physiol.*, 61:796–802, 1978.

Woodward et al., "Factors that influence the activity of 2,4-dihydroxy-7-methoxy-2H-1,4-benzoxazin-3(4H)-one on *Erwinia* species in growth assays," *Plant Physiol.*, 61:803–805, 1978.

Wright et al., "The maize auxotrophic mutant *orange pericarp* is defective in duplicate genes for tryptophan synthase β," *Plant Cell*, 4:711–719, 1992.

Wright et al., "The orange pericarp mutant of maize is a tryptophan auxotroph," Source unknown.

Wright, "Fluoroindole resistance of orange pericarp," Source unknown.

Co-pending U.S. Patent Application Serial No. 08/113,561 filed Aug. 25, 1993.

Co-pending U.S. Patent Application Serial No. 98/763,704 filed Dec. 9, 1996.

* cited by examiner

ACCAGCCATACCAGAAGAC - *Mu element* - CCAGAAGACAGGATGAAGG
bx1::Mu
CAACGTGTCCCTCCTCGGC - *Mu element* - CTCCTCGGCCGGTTCAACC
bx3::Mu
FIG. 1C
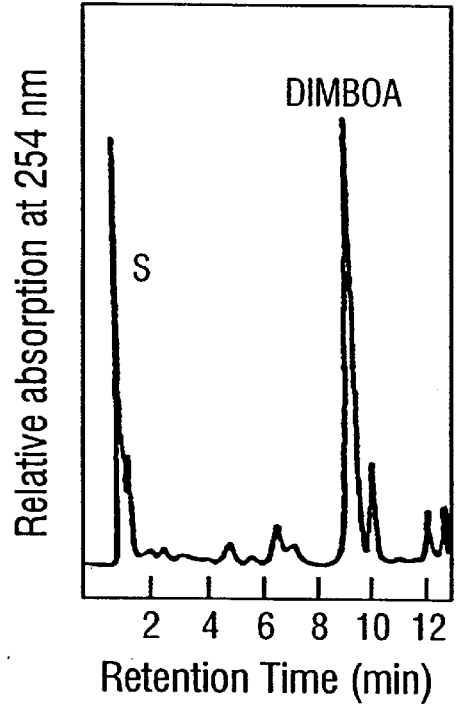
FIG. 2A
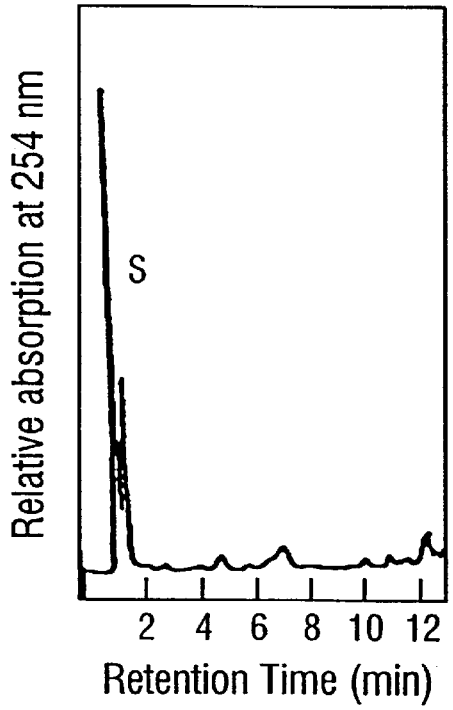
FIG. 2B

Bx1

GAPDH

MAIZE DIMBOA BIOSYNTHESIS GENES

This application is a continuing application of U.S. Provisional Patent Application Ser. No. 60/040,513, filed Mar. 13, 1997.

BACKGROUND OF THE INVENTION

1. Field of the Invention

The present invention relates generally to the field of plant resistance to insects and pathogens. More specifically, it relates to plant genes of benzoxazinone biosynthesis.

2. Description of Related Art

Plants protect themselves against infestation with pathogens by a number of chemical defense mechanisms. In this regard, especially the secondary metabolites of plants can be mentioned. Among these chemically very heterogeneous compounds there are many substances which have a poisonous or deterrent effect on animals such as insects and on microorganisms. The synthesis of these defense substances can be regulated in different ways. It is often only induced in case of infestation with pathogens or in specific tissues of the plant or only during a specific developing stage of the plant.

Benzoxazinones are a class of secondary metabolites found almost exclusively in gramineae. DIMBOA (2,4-dihydroxy-7-methoxy-1,4benxoxazin-3-one) and DIBOA (2,4-dihydroxy-4-benzoxazin-3-one) are the primary benzoxazinones both found in maize. DIBOA is the main benzoxazinone occurring in rye, whereas DIMBOA is the main benzoxazinone occurring in wheat and maize (Walross et al., 1959). DIBOA and DIMBOA have been shown to have a broad spectrum of effects on insects and microorganisms. A positive correlation of the concentration of DIMBOA and resistance to (i) the fungus *Helminthosporium turcicum*, which causes of the Northern Leaf Blight disease (Couture et al., 1971), (ii) infestation with the maize plant louse *Rhophalosiphum maydis* (Long et al., 1977), (iii) *Diplodia maydis* (stalk rot), and (iv) especially to the European corn borer *Ostrinia nubilalis* (Campos et al., 1989), have been found in maize. The same applies to the resistance of wheat to the fungus *Puccinia graminis* (Long et al., 1977). In particular, the European corn borer causes great damage every year in all areas in which corn is cultivated. For example, in the USA the damage amounts to about 500 million dollars and can be controlled by pesticides only to a limited extent.

The effect of DIMBOA on larvae of the European corn borer has been the topic of a number of investigations. For instance, food containing a large amount of DIMBOA is refused by the corn borer larvae in favor of food without DIMBOA, whereas in the case of an exclusive DIMBOA diet, the amount of food taken is increased. The increase of the amount of food is necessary for the larvae, since DIMBOA leads to an obstruction of the proteolytic activity in the digestive tract of the larvae. Thus, plants containing DIMBOA are avoided by the European corn borer, or, if these plants are infested, the brood starves (Cuevas et al., 1990).

The accumulation of benzoxazinones in maize is absent in lines homozygous for a mutation known as bx1 (Hamilton, 1964). Homozygous bx1 plants grow normally, but are extremely susceptible to the above mentioned pathogen infections, further implicating DIMBOA and related compounds in a resistance mechanism. Furthermore, the mutant plants are not auxotrophs for tryptophan, a DIMBOA precursor, indicating that the mutation is specific for a gene involved in the DIMBOA biosynthesis pathway.

Genetic analysis with monosome lines and translocation lines has resulted in the localization of the Bx1 locus on the short chromosome arm of chromosome 4 near Rp4 (Simcox et al., 1985). Bx1 mapped with the Recombinant Inbred System to the short arm of chromosome 4, and within the limits of the method, was located at exactly the same map position as Bx2 (Burr et al., 1991). Further, genes which influence the benzoxazinone concentrations as drastically as the Bx1 genes are not known. Investigations of inbred lines led to an estimation of 7 additional loci associated with benzoxazinone biosynthesis, although the loci only condition the formed amount of benzoxazinone (Dunn et al., 1981). The available genetic data indicates that the Bx1 gene is a key enzyme in DIMBOA biosynthesis.

In one study, the Bx1 gene was reported to have been cloned (Frey et al., WO 93/2244). In this case, a cytochrome p450 gene was identified which genetically mapped near the Bx1 locus. The suggestion that this was Bx1 was based upon the close genetic linkage of the cloned gene to Bx1, and also because Bx1 was believed to be a cytochrome p450 gene. Upon further analysis of the reported bx1 mutant, however, it was realized that this was not the Bx1 locus and was instead a secondary gene involved in DIMBOA biosynthesis (Frey et al. 1995).

There has, therefore, been a failure in the art to identify the key gene in the biosynthesis of benzoxazinones in maize, Bx1. Still further, the art has failed in identifying methods and compositions for the production of transgenic plants having enhanced benzoxazinone biosynthesis as a result of having been transformed with one or more genes of the benzoxazinone biosynthetic pathway, for example, Bx1. Such plants are needed because, even in plants naturally producing DIMBOA or DIBOA, benzoxazinone levels are highest early in development and fall significantly as the plant ages. Thus DIMBOA mediated resistance to ECB is limited to the first brood of the insect, whereas infestation with the second brood takes place when the DIMBOA concentration in the plant has dropped (Niemeyer et al., 1988). Therefore, while the high levels of DIMBOA in young plants serve as an effective agent in minimizing the damage caused by insects and other deleterious agents, the limited levels of DIMBOA biosynthesis in older tissues diminishes its protective effects.

Elucidation of the DIMBOA biosynthetic pathway, as well as the cloning of genes involved in the pathway, would allow for the production of transgenic plants with enhanced profiles of DIMBOA biosynthesis. Such plants would have improved resistance to a broad spectrum of insects, chemicals and pathogens and represent a significant advance to agriculture. To date, however, reaching the goal of producing such plants has been severely limited by the general lack of information regarding the DIMBOA biosynthetic pathway and the genes which encode enzymes in the pathway.

SUMMARY OF THE INVENTION

In one aspect of the invention, transgenic plants are provided having enhanced levels of benzoxazinone biosynthesis, and concomitantly, resistance to various pests, pathogens and chemical agents. One aspect in achieving this goal, which is provided by the current invention, is an isolated Bx1 polypeptide. The Bx1 polypeptide may, in particular embodiments of the invention, be a maize polypeptide. The polypeptide may comprise a transit peptide having the amino acid sequence set forth as residue 1 to about residue 85–100 of SEQ ID NO:2. The polypeptide may further have the full length amino acid sequence as set forth in SEQ ID NO:2. The polypeptide may still further comprise a transit peptide heterologous to said Bx1 transit polypeptide. In particular embodiments of the invention, the transit peptide may be selected from the group consisting of chlorophyll a/b binding protein transit peptide, small subunit of ribulose bisphosphate carboxylase transit peptide, EPSPS transit peptide and dihydrodipocolinic acid synthase transit peptide.

In another aspect of the invention, an isolated nucleic acid encoding a Bx1 polypeptide is provided. The isolated nucleic acid encoding a Bx1 polypeptide may be a maize polypeptide. The isolated nucleic acid may further comprise a nucleic acid segment encoding a transit peptide having the amino acid sequence set forth as residue 1 to about residue 85–100 of SEQ ID NO:2. The isolated nucleic acid may have the nucleic acid sequence as set forth in SEQ ID NO:1.

In yet another aspect of the invention, an expression cassette is provided comprising a DNA sequence encoding a Bx1 polypeptide linked operably to a promoter functional in a plant cell. The expression cassette may encode a Bx1 polypeptide with an amino acid sequence as set forth in SEQ ID NO:2. In particular embodiments the expression cassette further comprising a selectable marker gene. The expression cassette may further comprise plasmid DNA, and may still further comprise a promoter functional in a monocot.

In still yet another aspect of the invention, an expression cassette comprising a benzoxazinone biosynthesis gene may be transformed into a monocotyledonous plant cell of a plant selected from the group consisting of wheat, maize, rye, tobacco, cotton, rice, sorghum, millet, sugarcane, tomato and potato. Said expression cassette may further posses a promoter functional in maize. In particular embodiments, the promoter is not functional in seed. Any promoter may potentially be used with the invention, for example, a CaMV 35S, CaMV 19S, nos, Adh, actin, histone, ribulose bisphosphate carboxylase, R-allele, root cell, α-tubulin, ABA-inducible, turgor-inducible, rbcS, corn sucrose synthetase 1, corn alcohol dehydrogenase 1, corn light harvesting complex, corn heat shock protein, pea small subunit RuBP carboxylase, Ti plasmid mannopine synthase, Ti plasmid nopaline synthase, petunia chalcone isomerase, bean glycine rich protein 1, CaMV 35s transcript, Potato patatin, actin, cab, PEPCase or S-E9 small subunit RuBP carboxylase promoter. In particular embodiments, the DNA of the expression cassette is oriented antisense to said promoter, thereby eliminating or decreasing the synthesis of benzoxazinones in plants having the expression cassette.

Still yet another aspect of the invention provides a method for increasing the resistance of a plant to pest infestation. The method comprises stably transforming a starting plant cell with an expression cassette comprising a DNA sequence encoding a Bx1 polypeptide operably linked to a promoter functional in a plant cell and regenerating the transformed cell into a fertile transgenic plant which produces plant cells in which the Bx1 polypeptide is expressed in an amount effective to increase the benzoxazinone content of the transformed cell as compared to a starting plant cell, whereby the resistance of said fertile transgenic plant to pest infestation is increased. In the method, the benzoxazinone can be 2,4-dihydroxy-7-methoxy-1,4-benzoxazin-3-one. In particular embodiments of the invention, the pest infestation is selected from the group consisting of *Helminthosporium turcicum, Rhophalosiphum maydis, Diplodia maydis* and *Ostrinia nubilalis*. In still further embodiments, the starting plant cell is derived from a monocot or dicot. The starting plant cell may be derived from a plant selected from the group consisting of wheat, maize, rye, tobacco, cotton, rice, sorghum, millet, sugarcane, tomato and potato.

In particular embodiments of the invention, the stably transformed starting plant cell may be transformed with a DNA encoding a polypeptide selected from the group consisting of Bx1, Bx2, Bx3, Bx4 and Bx5. Any method of transformation may be used in the invention, particularly electroporation, microinjection, microprojectile bombardment and liposomal encapsulation. The method may still further comprise stably transforming said starting plant cell with a selectable marker gene. Any selectable marker gene may be used, for example, a marker selected from the group consisting of phosphinothricin acetyltransferase, glyphosphate resistant EPSPS, aminoglycoside phosphotransferase, hygromycin phosphotransferase, dalapon dehalogenase, bromoxynil resistant nitrilase and anthranilate synthase. The method further may comprise breeding the fertile transgenic plant to yield a progeny plant that has an increase in the pest resistance while maintaining functional agronomic characteristics relative to a plant regenerated with and bred from said starting plant cell. The method may still further comprise collecting seed from said fertile transgenic plant.

In still yet another aspect of the invention, a method for increasing benzoxazinone production in a plant is provided comprising stably transforming a starting plant cell with an expression cassette comprising a DNA sequence encoding a Bx1 polypeptide linked operably to a promoter functional in a plant cell and regenerating the transformed cell into a fertile transgenic plant which produces plant cells in which the Bx1 polypeptide is expressed in an amount effective to increase the benzoxazinone content of said transformed cell as compared to said starting plant cell. The benzoxazinone produced in the method may be 2,4-dihydroxy-7-methoxy-1,4-benzoxazin-3-one. In particular embodiments of the invention, the increase in 2,4-dihydroxy-7-methoxy-1,4-benzoxazin-3-one is about 2-fold to about 50-fold.

In still yet another aspect of the invention, a transgenic plant cell is provided comprising an exogenous Bx1 transgene linked operably to a promoter functional in said plant cell. The transgenic plant cell may comprise, for example, a promoter selected from the group consisting of a CaMV 35S, CaMV 19S, nos, Adh, actin, histone, ribulose bisphosphate carboxylase, R-allele, root cell, α-tubulin, ABA-inducible, turgor-inducible, rbcS, corn sucrose synthetase 1, corn alcohol dehydrogenase 1, corn light harvesting complex, corn heat shock protein, pea small subunit RuBP carboxylase, Ti plasmid mannopine synthase, Ti plasmid nopaline synthase, petunia chalcone isomerase, bean glycine rich protein 1, CaMV 35s transcript, Potato patatin, actin, cab, PEPCase or S-E9 small subunit RuBP carboxylase promoter. In particular embodiments of the invention, the transgenic plant cell is a monocotyledonous plant selected from the group consisting wheat, maize, rye, tobacco, rice, sorghum, millet, and sugarcane. In other embodiments of the invention, the plant cell is a dicot selected from the group consisting of tomato, potato, tobacco and cotton. The transgenic plant cell may further comprise at least one transgene encoding a polypeptide selected from the group consisting of Bx1, Bx2, Bx3, Bx4 and Bx5. The transgenic plant cell may further comprise at least one selectable marker gene. Still yet another aspect of the invention is a plant comprising said transgenic plant cell.

Still yet another aspect of the invention provides a fertile transgenic *Zea mays* plant having an increased resistance to pest infestation. In particular embodiments of the invention, this plant is stably augmented by a transgene encoding a Bx1 polypeptide, wherein said transgene is transmitted through a complete normal sexual cycle of the transgenic plant to the next generation. The invention also relates to seed derived from this plant and any subsequent progeny of a plant derived from this seed, wherein the progeny inherit the Bx1 comprising transgene. The pest infestation may, in particular embodiments, be selected from the group consisting of *Helminthosporium turcicum, Rhophalosiphum maydis, Diplodia maydis* and *Ostrinia nubilalis*.

Still yet another aspect of the invention provides a method for decreasing benzoxazinone production in a plant. In particular embodiments of the invention the method comprises stably transforming a starting plant cell with an expression cassette comprising a DNA sequence encoding an antisense Bx1 mRNA linked operably to a promoter functional in a plant cell; and regenerating the transformed cell into a fertile transgenic plant which produces plant cells in which the Bx1 polypeptide is inhibited to an extent that that the benzoxazinone content of said transformed cell is decreased when compared to the starting plant cell. The method may utilize plant tissue specific promoters in order to cause a tissue specific decrease of benzoxazinones.

Still yet another aspect of the invention is to provide a DNA sequence which contributes resistance to the European corn borer and other pests to plants which naturally do not have such a resistance or loose this resistance during aging. In a preferred embodiment, the benzoxazinone gene may be a maize Bx1 gene. Insofar as the Bx1 gene is present in the genome of gramineae, the invention may include a Bx1 gene from the genome of the gramineae, for example, from maize, wheat and rye. In another aspect of the invention, this plant may further comprise a transgene having one or more gene selected from the group consisting of Bx2, Bx3, Bx4 and Bx5.

Still yet another aspect of the invention provides a vector containing a DNA sequence for transforming plants. The Bx1 gene DNA sequence, as well as the Bx1 cDNA sequence, the alleles and derivatives thereof may be inserted in a recombinant vector comprising an appropriate promoter region. Such appropriate promoters are specifically disclosed herein. Still further, vectors may be prepared having any one or more of the genes selected from the group consisting of Bx1, Bx2, Bx3, Bx4 and Bx5.

Still yet another aspect of the invention provides a method for introducing or improving resistance to the European corn borer in plants. This effect may be realized by transforming plants with one or more genes of benzoxazinone biosynthesis, thereby enhancing DIMBOA biosynthesis. The invention also provides a method for introducing tolerance to herbicides in plants, wherein the effect may be realized by transforming plants with one or more genes of benzoxazinone biosynthesis, thereby enhancing DIMBOA biosynthesis.

Still yet another aspect of the invention provides a DNA sequence of SEQ ID NO:1, representing the Bx1 cDNA which encodes a protein in the biosynthesis of benzoxazinones. Also included in the invention are the alleles and derivatives of said DNA sequence, as it will be understood that the scope of the invention includes the allelic variants and derivatives of the Bx1 gene, provided that the protein encoded by these allelic variants and derivatives have the same function as the protein encoded by the Bx1 gene.

The Bx1 cDNA enables the isolation of genomic sequences containing the Bx1 gene including putative cis-regulatory sequences. This may be achieved by conventional gene technological methods, for example, by a process comprising the steps of restriction fragment size fractionation of genomic DNA from a plant capable of producing benzoxazinones such as a wild-type maize line, isolation of DNA size fragments presumably containing the Bx1 gene, cloning of these DNA size fragments presumably containing the Bx1 gene into appropriate host cells, e.g. *Escherichia coli*, by appropriate cloning vectors such as lambda phage vectors, and finally selection and isolation of positive clones by probing with labeled Bx1 cDNA.

The DNA sequence comprising the Bx1, B2, Bx3, Bx4, and Bx5 gene or cDNA sequence, as well as the alleles and derivatives thereof, may be introduced by gene transfer methods into plants for the production of benzoxazinones. The Bx1, Bx2, Bx3, Bx4, and Bx5 gene or cDNA sequences, the alleles and derivatives thereof are preferably introduced with appropriate promoters, particularly in recombinant vectors as described herein into plants for the controlled and regulated production of benzoxazinones. A variety of plants may be used for this purpose, including agronomically useful plants, horticultural plants and ornamental plants, which either do not produce benzoxazinones by nature, produce benzoxazinones only in low amounts or produce benzoxazinones only in a specific developmental stage, e.g., the juvenile stage. Preferred plants are gramineae, with *Zea mays* being particularly preferred.

By using the Bx1 cDNA or the Bx1 gene DNA sequence as well as other Bx genes, the alleles and derivatives thereof, it is possible to contribute or improve resistance to plants, plant parts and plant products thereof which naturally either do not produce benzoxazinones, produce benzoxazinones only in low amounts or produce benzoxazinones only in specific developmental stage, e.g. the juvenile stage. By gene technological transfer of the Bx1 cDNA or the Bx1 gene, the alleles and derivatives thereof, the formation of benzoxazinones in plants may be induced and controlled respectively. Plants which naturally do not produce benzoxazinones can increase their chemical defense potential. The benzoxazinone synthesis period can be prolonged in gramineae (cereals) such that the expression profile of the Bx1 gene is changed to protect the maturing plant, for example, against the second brood of the European corn borer.

As explained above, the presence of an intact Bx1 gene in plants correlates with the detoxification of herbicides like atrazine and simazine. That is, the Bx1 cDNA or the Bx1 gene, and thus the Bx1 gene product, contributes tolerance to herbicides in plants. Therefore, the description above of the Bx1 gene mediated resistance of plants to the European corn borer and other pests via the production of benzoxazinones is likewise applicable to the Bx1 gene mediated tolerance of plants to herbicides.

Thus, another embodiment of the present invention provides a process for the production of plants, plant parts and plant products tolerant to herbicides, which comprises the step of introducing a DNA material into plants by means of gene technological methods.

Still yet another aspect of the invention comprises the use of antisense technology to inhibit the synthesis of benzoxazinones. It is contemplated that such inhibition of benzoxazinone synthesis could be used to facilitate the transformation of plant species. In particular embodiments of the invention, this may include inhibition of benzoxazinone biosynthesis to facilitate Agrobacterium-mediated transformation in maize.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A, 1B, and 1C: Structure and Chromosomal Location of the Bx genes. (FIG. 1A) Schematic representation of the Bx gene cluster on chromosome 4. Genetic distance is indicated in centi Morgans. (FIG. 1B) Exon/intron structure of Bx1 to Bx5. Exons are represented by boxes. Translation start and stop codons and poly(A) addition sites are shown. The insertion of a Mu element in the bx1::Mu allele is designated by an arrow. The deletion in the bx1 standard allele is indicated, it comprises nucleotides 1366 to 2289 of the published sequence. The distance of Bx1 to Bx2 (2490 bp) is not drawn to scale. The complete sequences of the genes have been deposited in the EMBL data bank (Accession numbers: Bx2: Y11368, Bx3: Y11404, Bx4: X81828, Bx5: Y11403). (FIG. 1C) The insertion sites of Mu in bx1::Mu is shown. The characteristic 9-bp host sequence duplication associated with Mu insertion is underlined with an arrow. In bx1::Mu the insertion occurred at position 1826.

FIGS. 2A, 2B, 2C, 2D, 2E, and 2F: Detection of Metabolites of the DIMBOA Pathway by HPLC. Metabolites are indicated at the position of chromatographic peaks. S represents the solvent peak. (FIG. 2A and FIG. 2B) Feeding of the bx1 standard mutant seedling shoots with 1 mM indole (FIG. 2A) or 1 mM tryptophan (FIG. 2B). One gram of seedling material was extracted and analyzed on a Merck LiVhroCART RP-18 HPLC column (4×125 mm). Elution was for 5 min under isocratic conditions with solvent A ($H_2O$/HOAc, 9:1) followed by a linear gradient from 100% solvent A to 100% B (MeOH/H2O/HOAc, 70:27:3) over 7 min. (FIGS. 2C, 2D, 2E and 2F) Analysis of maize p450 enzymes expressed in yeast microsomes. Reaction mixtures of 0.2 ml contained 50 mM K-Pi pH 7.5. 0.8 mM NADPH, 0.1 mM to 0.5 mM of the respective substrates, and 1 mg microsomal protein. Incubation was for 30 min at 25° C. HPLC analysis was as described above. (FIG. 2C) Bx2 microsomes incubated with indole, (FIG. 2D) Bx3 microsomes incubated with indolin-2-one, (FIG. 2E) Bx4 microsomes incubated with 3-hydroxy-indolin-one, (FIG. 2F) Bx5 microsomes incubated with HBOA.

DETAILED DESCRIPTION OF THE INVENTION

Figure 1A:
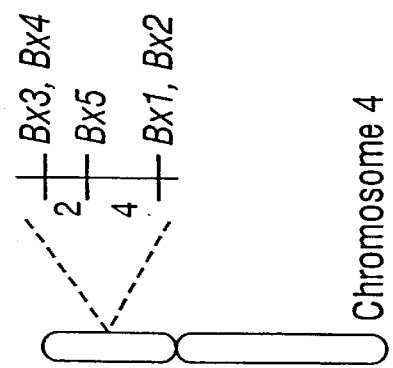
Figure 1B:
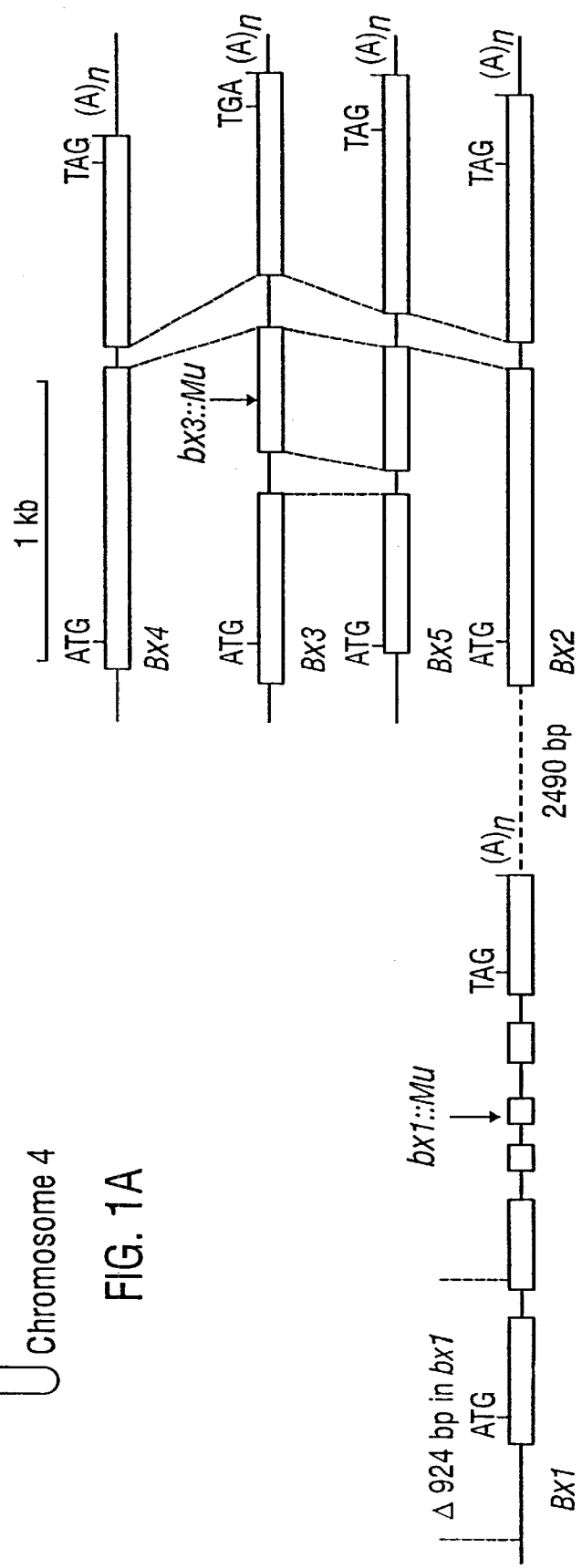

In an effort to provide the means for producing plants with enhanced resistance to a broad spectrum of insects, chemical agents, and other deleterious agents, the current inventors have sought to understand the biosynthetic pathway of benzoxazinones. This has resulted in a clear understanding of the genes involved in this pathway. Further, it has resulted in the cloning of the Bx1 gene, which is thought to have the largest single effect on the synthesis of benzoxazinones. These findings provide for the first time, the understanding necessary for the production of transgenic plants with enhanced expression profiles of benzoxazinone biosynthesis.

Therefore, one embodiment of the invention provides an expression cassette with a DNA sequence encoding a Bx1 polypeptide linked operably to a promoter functional in a plant cell. The expression cassette may include a polypeptide with an amino acid sequence as set forth in SEQ ID NO:2. In particular embodiments the expression cassette may further comprise a selectable marker gene, plasmid DNA, and a promoter functional in a monocot. The expression can further comprise a promoter functional in maize. Examples of some promoters that may be used with an expression cassette of the invention include CaMV 35S, CaMV 19S, nos, Adh, actin, histone, ribulose bisphosphate carboxylase, R-allele, root cell promoter, α-tubulin, ABA-inducible promoter, turgor-inducible promoter, rbcS, corn sucrose synthetase 1, corn alcohol dehydrogenase 1, corn light harvesting complex, corn heat shock protein, pea small subunit RuBP carboxylase, Ti plasmid mannopine synthase, Ti plasmid nopaline synthase, petunia chalcone isomerase, bean glycine rich protein 1, CaMV 35s transcript, Potato patatin, actin, cab, PEPCase and S-E9 small subunit RuBP carboxylase promoter. Examples of monocots may include wheat, maize, rye, tobacco, cotton, rice, sorghum, millet, sugarcane, tomato and potato. In particular embodiments of the invention a promoter which is not functional in seed may be used. An expression cassette may further be made wherein DNA is oriented antisense to said promoter.

In another embodiment of the invention, a fertile transgenic *Zea mays* plant is provided with increased benzoxazinone production, the genome of which is stably augmented by a transgene encoding a Bx1 polypeptide, wherein the transgene is transmitted through a complete normal sexual cycle of the transgenic plant to the next generation. The invention also comprises a seed derived from this plant, and any subsequent progeny plant derived from the seed of the plant.

In still another embodiment of the invention, a method is provided for decreasing benzoxazinone production. In particular embodiments, this method comprises stably transforming a starting plant cell with an expression cassette comprising a DNA sequence encoding an antisense Bx1 mRNA linked operably to a promoter functional in a plant cell; and regenerating the transformed cell into a fertile transgenic plant which produces plant cells in which the Bx1 polypeptide is inhibited to an extent that that the benzoxazinone content of said transformed cell is decreased when compared to said starting plant cell. In particular embodiments, the method comprises using a plant tissue specific promoter. Decreasing benzoxazinone biosynthesis in this manner may be used in facilitating transformation with Agrobacterium. It may further be used to eliminate benzoxazinones from specific types of tissue, such as the kernel.

The Bx1 cDNA provided by the invention is defined by means of DNA sequence determinations, and thereby allows one to deduce the amino acid sequence of the protein encoded by either the Bx1 cDNA or the Bx1 gene. It will be understood that allelic variations exist. These variations may include deletions, substitutions, insertions, inversions or additions of a nucleotide or nucleotides in the overall DNA sequence of SEQ ID NO:1, or in a genomic DNA sequence comprising a Bx1 allele. Furthermore, methods exist in the genetic engineering technology for the preparation of various derivatives of the DNA sequence of SEQ ID NO:1, such as deletions, substitutions, additions, or replacements, for example by site-directed mutagenesis. Other DNA sequences, such as signal sequences or regulatory elements, may be added to the 5'-end or the 3'-end of the DNA sequences of SEQ ID NO:1, or may be added to the 5'-end or the 3'-end of the Bx1 coding region. In particular, one may wish to add, alter, delete or otherwise change sequences at the 5' end of a Bx1 gene which code for transit peptides, thereby directing the gene product of the Bx1 gene or another benzoxazinone biosynthesis gene to a particular cellular location. Alternatively, said other DNA sequences may exchange sequences upstream or downstream of the coding sequence of either a cDNA clone or genomic clone of the Bx1 gene. Still further, the present disclosure would allow one to isolate alleles of the benzoxazinone biosynthesis genes described herein from species which are related to maize, for example, members of the gramineae.

The genes described herein can be assayed for expression in vivo through Northern analysis. Techniques for Northern analysis are well known in the art. The technique allows one to detect the messenger RNA expressed by a particular gene and thus the expression level of that particular gene. The analysis can be directed to specific tissue types such as root, pollen and leaf, as well as to particular periods of development. In cases where the exogenous gene being analyzed is normally expressed within the native plant, determination of expression of the foreign gene may be based upon the rate and tissue specificity of expression, as well as variations in gene expression due to different developmental periods or environmental factors.

Positive selection of transformed plants may be carried out by the root staining method. Staining of root squashes of the plant with FeCl$_3$ produces a blue complex if benzoxazinones are present, and this indicates the presence of benzoxazinones in the plant (Hamilton, 1964; Long et al., 1974; and Sullivan et al., 1974).

Methods for identification of transposon tagged alleles are well known in the art. One method for the identification of transposable elements is by Southern analysis. However, this is only possible if the number of elements present does not exceed the resolution capacity of the method. Commonly, when this is the case, the number of transposons may be decreased by outcrossing to maize lines lacking the transposable element system. The Mu tagged allele of the bx1 mutant may be tracked during outcrossing using a linked genetic marker. A standard gel system for nucleic acids with a high potential of resolution may also be used to reduce the complexity of the tagged sequences prior to the analysis.

The introduction of the DNA sequence comprising the Bx1 cDNA or the Bx1 gene, the alleles and derivatives thereof may be accomplished according to standard transformation techniques including calcium phosphate precipitation, polyethylene glycol treatment, electroporation, particle gun bombardment and Agrobacterium-mediated gene transfer, which are specifically disclosed herein below.

I. Definitions

The following words and phrases have the meanings set forth below.

Bx Gene: The set of genes comprising Bx1, Bx2, Bx3, Bx4 and Bx5, each of which catalyze steps in the biosynthesis of DIBOA from indole-3-glycerophosphate.

Expression: The combination of intracellular processes, including transcription and translation undergone by a coding DNA molecule such as a structural gene to produce a polypeptide.

Expression Cassette: A nucleic acid segment comprising at least a first gene one desires to have expressed in a host cell and the necessary regulatory elements for expressing the gene in the host cell. Preferred regulatory elements for use with the invention include promoters, enhancers and terminators. It may also be desirable to include on the expression cassette a nucleic acid segment encoding an appropriate transit peptide, as is described below. The expression cassette may contained and propagated in any suitable cloning vector, for example, a plasmid, cosmid, bacterial artificial chromosome, or yeast artificial chromosome. The whole vector DNA may be used to transform a host cell, or alternatively, the expression cassette may be isolated from the vector and then used for transformation.

Promoter: A recognition site on a DNA sequence or group of DNA sequences that provide an expression control element for a structural gene and to which RNA polymerase specifically binds and initiates RNA synthesis (transcription) of that gene.

Regeneration: The process of growing a plant from a plant cell (e.g., plant protoplast or explant).

Structural gene: A gene that is expressed to produce a polypeptide.

Sexually compatible: The descriptive term for the condition which exists when two plants are capable of being crossed to produce fertile progeny.

Transformation: A process of introducing an exogenous DNA sequence (e.g., a vector, a recombinant DNA molecule) into a cell or protoplast in which that exogenous DNA is incorporated into a chromosome or is capable of autonomous replication.

Transformed cell: A cell whose DNA has been altered by the introduction of an exogenous DNA molecule into that cell.

Transgenic cell: Any cell derived or regenerated from a transformed cell or derived from a transgenic cell. Exemplary transgenic cells include plant calli derived from a transformed plant cell and particular cells such as leaf, root, stem, e.g., somatic cells, or reproductive (germ) cells obtained from a transgenic plant.

Transgenic plant: A plant or progeny of any subsequent generation derived therefrom, of a transformed plant cell or protoplast, wherein the plant DNA contains an introduced exogenous DNA molecule not originally present in a native, non-transgenic plant of the same strain. The transgenic plant may additionally contain sequences which are native to the plant being transformed, but wherein the "exogenous" gene has been altered by gene technological means in order to alter the level or pattern of expression of the gene. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant, and that usage will be followed herein.

Progeny: Any subsequent generation, including the seeds and plants therefrom, which is derived from a particular parental plant or set of parental plants.

Transit Peptide: A polypeptide sequence which is capable of directing a polypeptide to a particular organelle or other location within a cell.

Vector: A DNA molecule capable of replication in a host cell and/or to which another DNA segment can be operatively linked so as to bring about replication of the attached segment. A plasmid is an exemplary vector.

II. DIMBOA Biosynthesis in Maize

DIMBOA can be detected in maize seedling a few days after initiation of germination (Klun et al., 1967). Subsequently it can be found in all parts of the plant, though in varying quantities. The DIMBOA synthesis is limited to the juvenile stage and the content of DIMBOA is drastically lower in aging plants.

The synthesis of benzoxazinones in maize is correlated with the dominant gene Bx1 (benzoxazinless) (Hamilton, 1964). Since the DIMBOA content increases during germination and decreases with the age of the plant, and since the protein product of the Bx1 gene takes a considerable part in the metabolic pathway of this end product, it can be concluded that the Bx1 gene expression is developmentally regulated. On the condition that there is transcriptional control, the Bx1 transcript should be present in young roots and in young shoots of wild type lines (2–4 days after initiation of germination).

DIMBOA synthesis has some intermediates in common with the tryptophan biosynthetic pathway. Labeled tryptophan precursors such as anthranilic acid, ribose and indole have been shown to be incorporated into DIMBOA, whereas labeled tryptophan was not incorporated into DIMBOA, implicating indole as the formal branchpoint of the two pathways (Desai et al., 1996).

It is estimated that the DIMBOA concentration in maize seedlings to about 0.1% of the fresh weight. This value exceeds the total tryptophan content of the seedling by a factor of about 10–20 (Radwanski et al., 1995). Hence most of the metabolites of tryptophan pathway should be channeled into the secondary metabolic DIMBOA pathway. The Bx1 enzyme would catalyze the committing step in DIMBOA synthesis by generating sufficient free indole for the subsequent conversion by other DIMBOA biosynthesis enzymes. The synthesis of several other secondary metabolites in plants, like for example the indole glucosinates, anthranilate-derived alkaloids and tryptamine derivatives depends on the tryptophan pathway(Radwanski et al., 1995; Kutchan, 1995).

In bacteria, two subunits of tryptophan synthase A (TSA) and tryptophan synthase B (TSB) form the tight tryptophan synthase complex comprising two subunits each of the A and B subunits ($A_2B_2$). In plants, there is evidence in Arabidopsis that a similar heterosubunit complex exists, analogous to the prokaryotic $A_2B_2$ complex (Radwanski et al., 1995). As tryptophan is essential for the maize plant, TSB mutants do not survive the juvenile stages (Wright et al., 1992). Since the TSA mutants are viable, there cannot be only one maize gene encoding TSA activity. Duplicated genes in maize are quite common, likely due to allotetraploidy involved in evolution of the maize genome (Helentjaris et al., 1999). For example there are two TSB genes in maize (Wright et al., 1992).

The cDNA sequences of four maize cytochrome P450 genes have been previously reported (Frey et al., 1995; Genbank Accession Numbers: Y11368, Y11404, X81828, and Y11403). On the basis of amino acid homology, these genes have been grouped into the CYP71C subfamily of plant cytochrome P450 genes. These genes are strongly expressed in young maize seedlings, share an overall amino acid identity of 45 to 60%, are clustered on the short arm of chromosome 4 (FIG. 1A), and are probably derived by gene duplication (Frey et al., 1995). The developmental expression pattern of the genes in the young maize plants, occurring predominantly in tissues that are exposed to the environment (Frey et al., 1995), matches well with the defense related DIMBOA accumulation. This observation and the finding that all oxygen atoms of DIMBOA are incorporated from molecular oxygen, led to the speculation that these cytochrome P450 enzymes might be involved in the DIMBOA biosynthesis pathway. As shown herein, the four enzymes are indeed integrated in DIMBOA biosynthesis. The genes encoding these enzymes are therefore termed in the following Bx2, Bx3, Bx4, and Bx5, respectively (Frey et al., 1995; Genbank Accession numbers: Bx2: Y11368, Bx3: Y11404, Bx4: X81828, and Bx5: Y11403).

Figure 3:
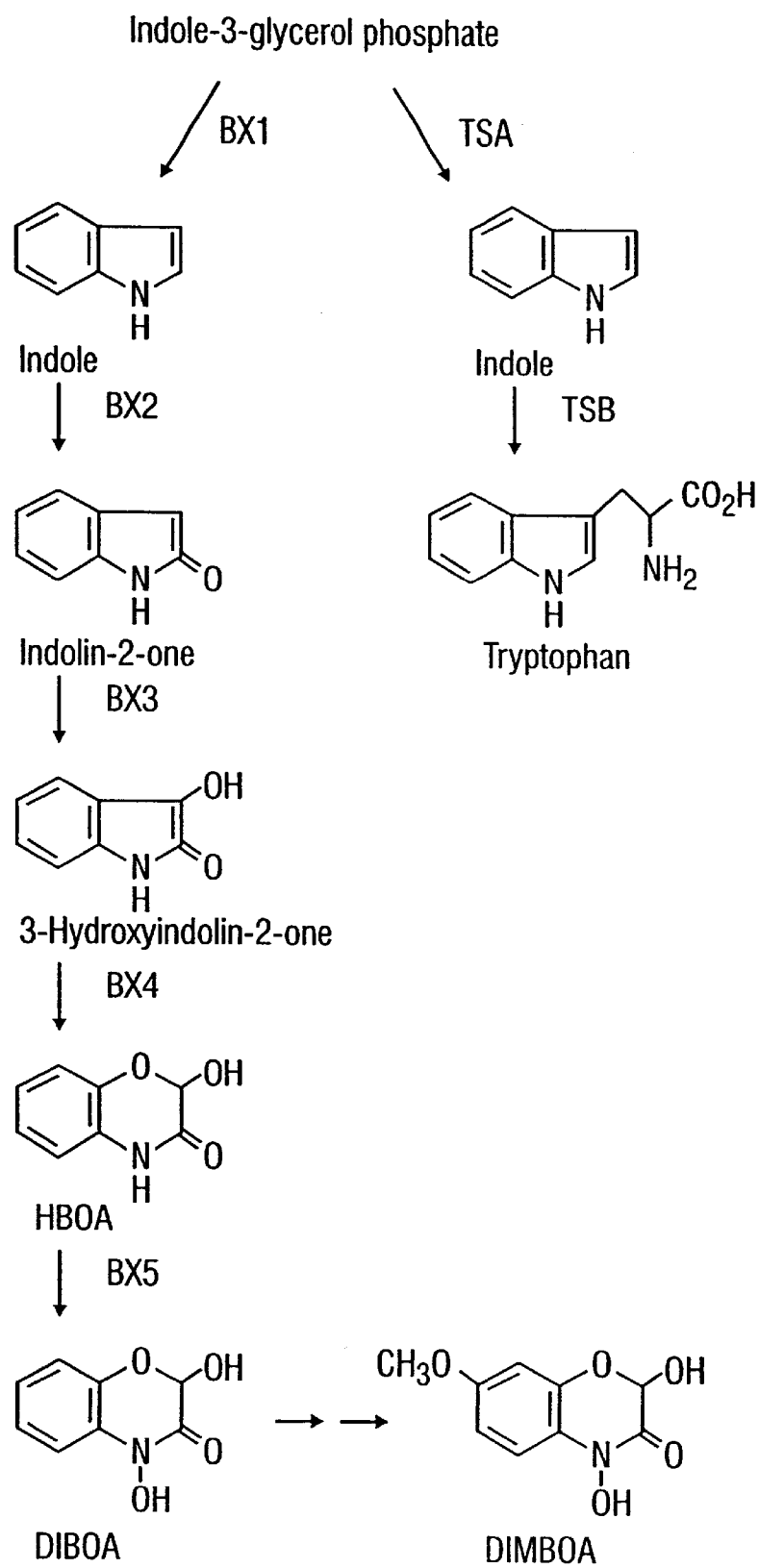
FIG. 3: Biosynthetic pathways to DIMBOA and tryptophan. Names of the gene products are indicated for each of the reactions. Bx1 represents a tryptophan synthase A activity. Bx2–Bx5 represent cytochrome p450-dependent monooxygenases of the CYP71C subfamily.

Bx1 and the four cytochrome P450 genes should represent a sufficient set of genes for the conversion of indole-3-glycerol phosphate to the secondary metabolite DIBOA (FIG. 3). The enzymatic activity required to convert DIBOA to DIMBOA are naturally present in maize plants. It is indicated that indole-3-glycerol phosphate is the branch-point from the tryptophan pathway. DIMBOA is the 7-methoxy derivative of DIBOA. The conversion of DIBOA to DIMBOA most likely requires two further enzymatic reactions. Hydroxylation of DIBOA by another cytochrome P450 enzyme followed by a methyltransferase reaction would be expected for the creation of DIMBOA. These enzymes which are probably present only in some gramineae remain to be isolated (Neimeyer et al., 1988).

III. Biological Functional Equivalents

Modification and changes may be made in the structure of the polypeptides of the present invention and DNA segments which encode them and still obtain a functional molecule that encodes a Bx1 protein or peptide with desirable characteristics. The following is a discussion based upon changing the amino acids of a protein to create an equivalent, or even an improved, second-generation molecule. In particular embodiments of the invention, mutated benzoxazinone biosynthesis proteins are contemplated to be useful for increasing the activity of the protein, and consequently increasing the production of bezoxazinones in a plant cell. The amino acid changes may be achieved by changing the codons of the DNA sequence, according to the codons given in Table 1.

TABLE 1

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |
| Lysine | Lys | K | AAA | AAG | | |
| Leucine | Leu | L | UUA | UUG | CUA | CUC | CUG | CUU |
| Methionine | Met | M | AUG | | | |
| Asparagine | Asn | N | AAC | AAU | | |
| Proline | Pro | P | CCA | CCC | CCG | CCU |
| Glutamine | Gln | Q | CAA | CAG | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU |
| Valine | Val | V | GUA | GUC | GUG | GUU |
| Tryptophan | Trp | W | UGG | | | |
| Tyrosine | Tyr | Y | UAC | UAU | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte et al., 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte et al., 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure. See, for example, Johnson et al., "Peptide Turn Mimetics" in *BIOTECHNOLOGY AND PHARMACY*, Pezzuto et al., Eds., Chapman and Hall, New York (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of Bx1, but with altered and even improved characteristics.

IV. Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of a immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, or cellular targeting signals. Fusion to a polypeptide that can be used for purification of the substrate-Bx1 complex could be used to further study the substrate-enzyme interaction.

V. Purification of Proteins

It may, in particular embodiments, be desirable to purify the Bx1 protein or other proteins involved in the benzoxazinone biosynthetic pathway. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; and isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

VI. Synthetic Peptides

The present invention also describes smaller Bx1-related peptides for use in various embodiments of the present invention. Because of their relatively small size, the peptides of the invention may also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

VII. Oligonucleotide Probes and Primers

Naturally, the present invention also encompasses DNA segments that are complementary, or essentially complementary, to the sequence set forth in SEQ ID NO:1. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of in SEQ ID NO:1 under relatively stringent conditions such as those described herein. Such sequences may encode the entire Bx1 protein or functional or non-functional fragments thereof.

Alternatively, the hybridizing segments may be shorter oligonucleotides. Sequences of 17 bases long should occur only once in the genome of most plant species and, therefore, suffice to specify a unique target sequence. Although shorter oligomers are easier to make, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47,48, 49, 50, 55, 60, 65, 70, 75, 80, 85, 90, 95, 100 or more base pairs will be used, although others are contemplated. Longer polynucleotides encoding 250, 500, 1000, 1212, 1500, 2000, 2500, or 3000 bases and longer are contemplated as well. Such oligonucleotides will find use, for example, as probes in Southern and Northern blots and as primers in amplification reactions.

Suitable hybridization conditions will be well known to those of skill in the art. In certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C. Formamide and SDS also may be used to alter the hybridization conditions.

One method of using probes and primers of the present invention is in the search for genes related to Bx1 and tryptophan synthase A from other species. The existence of benzoxazinones in species other than maize, and particularly in other members of the gramineae suggests that other homologs of Bx1 and tryptophan synthase A will be discovered in species other than maize. Normally, the target DNA will be a genomic or cDNA library, although screening may involve analysis of RNA molecules. By varying the stringency of hybridization, and the region of the probe, different degrees of homology may be discovered.

Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

VIII. Generating Antibodies Reactive With Bx1 Proteins

In another aspect, the present invention contemplates an antibody that is immunoreactive with a Bx1 molecule of the present invention, or any portion thereof. An antibody can be a polyclonal or a monoclonal antibody. In a preferred embodiment, an antibody is a monoclonal antibody. Means for preparing and characterizing antibodies are well known in the art (see, e.g., Howell and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a non-human animal including rabbits, mice, rats, hamsters, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing antigenic epitopes of the compounds of the present invention can be used to immunize one or more experimental animals, such as a rabbit or mouse, which will then proceed to produce specific antibodies against the compounds of the present invention. Polyclonal antisera may be obtained, after allowing time for antibody generation, simply by bleeding the animal and preparing serum samples from the whole blood.

It is proposed that the monoclonal antibodies of the present invention will find useful application in standard immunochemical procedures, such as ELISA and Western blot methods and in immunohistochemical procedures such as tissue staining, as well as in other procedures which may utilize antibodies specific to Bx1-related antigen epitopes. Additionally, it is proposed that monoclonal antibodies specific to a particular Bx protein of different species may be utilized in other useful applications.

In general, both polyclonal and monoclonal antibodies against Bx1 may be used in a variety of embodiments. For example, they may be employed in antibody cloning protocols to obtain cDNAs or genes encoding other Bx1 proteins. They may also be used in inhibition studies to analyze the effects of Bx1 related peptides in cells or plants. Anti-Bx1 antibodies will also be useful in immunolocalization studies to analyze the distribution of Bx1 during various cellular events or stages of development. A particularly useful application of such antibodies is in purifying native or recombinant Bx1 polypeptides, for example, using an antibody affinity column. The operation of all such immunological techniques will be known to those of skill in the art in light of the present disclosure.

Means for preparing and characterizing antibodies are well known in the art (see, e.g., Harlow and Lane, 1988; incorporated herein by reference). More specific examples of monoclonal antibody preparation are given in the examples below.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified Bx1 protein, polypeptide or peptide or cell expressing high levels of Bx1. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al., (1977). The use of electrically induced fusion methods is also appropriate (Goding, 1986).

Fusion procedures usually produce viable hybrids at low frequencies, around $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassay, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

IX. Genetic Analysis of Bx Transgenic Plants

One embodiment of the instant invention comprises a method for detecting variation in the expression of Bx genes. As used herein, the term "Bx gene" is meant to represent a gene of DIMBOA biosynthesis which includes Bx1, Bx2, Bx3, Bx4 and Bx5. This method may comprise determining that level of Bx protein or determining specific alterations in the expressed product. Obviously, this sort of assay has importance in the screening of transformants for potential insect resistance. Such assays may in some cases be faster, more accurate or less expensive than conventional insect feeding assays.

The biological sample may potentially be any type of plant tissue. Nucleic acid is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given plant with a statistically significant reference group of non-transformed control plants. Typically, the non-transformed control plants will be of a genetic background similar to the transformed plants. In this way, it is possible to detect differences in the amount or kind of Bx protein detected in various transformed plants.

A variety of different assays are contemplated in the screening of plants for particular Bx transgenes and associated exogenous elements. These techniques may in cases be used to detect for both the presence of the particular genes as well as rearrangements that may have occurred in the gene construct. The techniques include but are not limited to, fluorescent in situ hybridization (FISH), direct DNA sequencing, PFGE analysis, Southern or Northern blotting, single-stranded conformation analysis (SSCA), RNAse protection assay, allele-specific oligonucleotide (ASO), dot blot analysis, denaturing gradient gel electrophoresis, RFLP and PCR-SSCP.

(i) Primers and Probes

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process.

In preferred embodiments, the probes or primers are labeled with radioactive species ($^{32}P$, $^{14}C$, $^{35}S$, $^{3}H$, or other label), with a fluorophore (rhodamine, fluorescein), an antigen (biotin, streptavidin, digoxigenin), or a chemillumiscent (luciferase).

(ii) Template Dependent Amplification Methods

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in its entirety.

Briefly, in PCR, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

Another method for amplification is the ligase chain reaction ("LCR"), disclosed in EPO No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention, Walker et al., (1992).

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Davey et al., EPO No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, M. A., In: *PCR PROTOCOLS: A GUIDE TO METHODS AND APPLICATIONS*, Academic Press, N.Y., 1990; Ohara et al., 1989; each herein incorporated by reference in their entirety).

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu et al., (1989), incorporated herein by reference in its entirety.

(iii) Southern/Northern Blotting

Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished as described above.

(iv) Separation Methods

It normally is desirable, at one stage or another, to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989.

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder, 1982).

(v) Detection Methods

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by a labeled probe. The techniques involved are well known to those of skill in the art and can be found in many standard books on molecular protocols. See Sambrook et al., 1989. For example, chromophore or radiolabel probes or primers identify the target during or following amplification.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al, 1994). The present invention provides methods by which any or all of these types of analyses may be used. Using the sequences disclosed herein, oligonucleotide primers may be designed to permit the amplification of sequences throughout the Bx1 or other Bx genes that may then be analyzed by direct sequencing.

(vi) Kit Components

All the essential materials and reagents required for detecting and sequencing Bx1, Bx2, Bx3, Bx4, Bx5 and variants thereof may be assembled together in a kit. This generally will comprise preselected primers and probes. Also included may be enzymes suitable for amplifying nucleic acids including various polymerases (RT, Taq, Sequenase™ etc.), deoxynucleotides and buffers to provide the necessary reaction mixture for amplification. Such kits also generally will comprise, in suitable means, distinct containers for each individual reagent and enzyme as well as for each primer or probe.

(vii) Design and Theoretical Considerations for Relative Quantitative RT-PCR

Reverse transcription (RT) of RNA to cDNA followed by relative quantitative PCR (RT-PCR) can be used to determine the relative concentrations of specific mRNA species isolated from plants. By determining that the concentration of a specific mRNA species varies, it is shown that the gene encoding the specific mRNA species is differentially expressed.

In PCR, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR amplification is directly proportional to the starting concentration of the target before the reaction began. By determining the concentration of the amplified products of the target DNA in PCR reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundances of the specific mRNA from which the target sequence was derived can be determined for the respective tissues or cells. This direct proportionality between the concentration of the PCR products and the relative mRNA abundances is only true in the linear range of the PCR reaction.

The final concentration of the target DNA in the plateau portion of the curve is determined by the availability of reagents in the reaction mix and is independent of the original concentration of target DNA. Therefore, the first condition that must be met before the relative abundances of a mRNA species can be determined by RT-PCR for a collection of RNA populations is that the concentrations of the amplified PCR products must be sampled when the PCR reactions are in the linear portion of their curves.

The second condition that must be met for an RT-PCR experiment to successfully determine the relative abundances of a particular mRNA species is that relative concentrations of the amplifiable cDNAs must be normalized to some independent standard. The goal of an RT-PCR experiment is to determine the abundance of a particular mRNA species relative to the average abundance of all mRNA species in the sample.

Most protocols for competitive PCR utilize internal PCR standards that are approximately as abundant as the target. These strategies are effective if the products of the PCR amplifications are sampled during their linear phases. If the products are sampled when the reactions are approaching the plateau phase, then the less abundant product becomes relatively over represented. Comparisons of relative abundances made for many different RNA samples, such as is the case when examining RNA samples for differential expression, become distorted in such a way as to make differences in relative abundances of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR assay for plant tissue. The problems inherent in plant tissue samples are that they are of variable quantity (making normalization problematic), and that they are of variable quality (necessitating the co-amplification of a reliable internal control, preferably of larger size than the target). Both of these problems are overcome if the RT-PCR is performed as a relative quantitative RT-PCR with an internal standard in which the internal standard is an amplifiable cDNA fragment that is larger than the target cDNA fragment and in which the abundance of the mRNA encoding the internal standard is roughly 5–100 fold higher than the mRNA encoding the target. This assay measures relative abundance, not absolute abundance of the respective mRNA species.

Other studies may be performed using a more conventional relative quantitative RT-PCR assay with an external standard protocol. These assays sample the PCR products in the linear portion of their amplification curves. The number of PCR cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR assays can be superior to those derived from the relative quantitative RT-PCR assay with an internal standard.

One reason for this advantage is that without the internal standard/competitor, all of the reagents can be converted into a single PCR product in the linear range of the amplification curve, thus increasing the sensitivity of the assay. Another reason is that with only one PCR product, display of the product on an electrophoretic gel or another display method becomes less complex, has less background and is easier to interpret.

(viii) Chip Technologies

Specifically contemplated by the present inventors are chip-based DNA technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization. See also Pease et al. (1994); Fodor et al. (1991).

X. Immunoassays for Bx Gene Expression

Antibodies of the present invention can be used in characterizing the expression of Bx genes, through techniques such as ELISAs and Western blotting. This may provide a more efficient, accurate or cost effective method to screen plants transformed with Bx genes for relative rates of DIMBOA biosynthesis.

The use of antibodies of the present invention, in an ELISA assay is contemplated. For example, anti-Bx proteins are immobilized onto a selected surface, preferably a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of non-specific adsorption sites on the immobilizing surface and thus reduces the background caused by non-specific binding of antigen onto the surface.

After binding of antibody to the well, coating with a non-reactive material to reduce background, and washing to remove unbound material, the immobilizing surface is contacted with the sample to be tested in a manner conducive to immune complex (antigen/antibody) formation.

Following formation of specific immunocomplexes between the test sample and the bound antibody, and subsequent washing, the occurrence and even amount of immunocomplex formation may be determined by subjecting same to a second antibody having specificity for Bx proteins that differs from the first antibody. Appropriate conditions preferably include diluting the sample with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

To provide a detecting means, the second antibody will preferably have an associated enzyme that will generate a color development upon incubating with an appropriate chromogenic substrate. Thus, for example, one will desire to contact and incubate the second antibody-bound surface with a urease or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

XI. Antisense Constructs

Antisense treatments are one way of inhibiting benzoxazinone biosynthesis in a plant. Antisense technology may be used to "knock-out" the function of the Bx1 gene or other benzoxazinone biosynthesis gene, thereby decreasing or eliminating the expression of benzoxazinones a transformed plant cell or whole plant.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50–200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

XII. Expression Vectors

The present invention contemplates an expression vector comprising a polynucleotide of the present invention. Thus, in one embodiment an expression vector is an isolated and purified DNA molecule comprising a promoter operatively linked to a coding region that encodes a polypeptide of the present invention, which coding region is operatively linked to a transcription-terminating region, whereby the promoter drives the transcription of the coding region.

As used herein, the term "operatively linked" means that a promoter is connected to an coding region in such a way that the transcription of that coding region is controlled and regulated by that promoter. Means for operatively linking a promoter to a coding region are well known in the art.

In a preferred embodiment, the recombinant expression of DNAs encoding the Bx1 proteins of the present invention is preferable in gram-negative bacterium such as an *E. coli* or *Pseudomonas* spp. host cell. Promoters which function in high-level expression of target polypeptides in *E. coli* and other Gram-negative host cells are well-known in the art. Alternatively, mutagenized or recombinant Bx1 protein-encoding gene promoters may be engineered by the hand of man and used to promote expression of the novel gene segments disclosed herein.

Where an expression vector of the present invention is to be used to transform a plant, a promoter is selected that has the ability to drive expression in plants. Promoters that function in plants are also well known in the art. Useful in expressing the polypeptide in plants are promoters that are inducible, viral, synthetic, constitutive as described (Poszkowski et al., 1989; Odell et al., 1985), and temporally regulated, spatially regulated, and spatio-temporally regulated (Chau et al., 1989).

A promoter is also selected for its ability to direct the transformed plant cell's or transgenic plant's transcriptional activity to the coding region. Structural genes can be driven by a variety of promoters in plant tissues. Promoters can be near-constitutive, such as the CaMV 35S promoter, actin promoter, histone promoters, and ubiquitin promoters or tissue-specific or developmentally specific promoters affecting dicots or monocots. Such promoters are discussed in U.S. patent application Ser. No. 08/113,561, filed Aug. 25, 1993, which is specifically incorporated herein by reference.

Where the promoter is a near-constitutive promoter such as CaMV 35S, increases in polypeptide expression are found in a variety of transformed plant tissues (e.g., callus, leaf, seed and root). Alternatively, the effects of transformation can be directed to specific plant tissues by using plant integrating vectors containing a tissue-specific promoter.

An exemplary tissue-specific promoter is the lectin promoter, which is specific for seed tissue. The Lectin protein in soybean seeds is encoded by a single gene (Le1) that is only expressed during seed maturation and accounts for about 2 to about 5% of total seed mRNA. The lectin gene and seed-specific promoter have been fully characterized and used to direct seed specific expression in transgenic tobacco plants (Vodkin et al., 1983; Lindstrom et al., 1990.). Similar are the maize zein and globulin-1 promoters.

An expression vector containing a coding region that encodes a polypeptide of interest is engineered to be under control of the lectin promoter and that vector is introduced into plants using, for example, a protoplast transformation method (Dhir et al., 1991) or microprojectile bombardment (U.S. patent application Ser. No. 08/113,561, filed Aug. 25, 1993). The expression of the polypeptide is directed specifically to the seeds of the transgenic plant.

A transgenic plant of the present invention produced from a plant cell transformed with a tissue specific promoter can be crossed with a second transgenic plant developed from a plant cell transformed with a different tissue specific promoter to produce a hybrid transgenic plant that shows the effects of transformation in more than one specific tissue.

Exemplary tissue-specific promoters are corn sucrose synthetase 1 (Yang et al., 1990), corn alcohol dehydrogenase 1 (Vogel et al., 1989), corn light harvesting complex (Simpson, 1986), corn heat shock protein (Odell et al., 1985), pea small subunit RuBP carboxylase (Poulsen et al., 1986; Cashmore et al., 1983), Ti plasmid mannopine synthase (Langridge et al., 1989), Ti plasmid nopaline synthase (Langridge et al., 1989), petunia chalcone isomerase (Van Tunen et al., 1988), bean glycine rich protein 1 (Keller et al., 1989), CaMV 35s transcript (Odell et al., 1985) and Potato patatin (Wenzler et al., 1989). Preferred promoters are the cauliflower mosaic virus (CaMV 35S) promoter and the rice actin promoter.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the polypeptide coding region to which it is operatively linked.

Typical vectors useful for expression of genes in higher plants are well known in the art and include vectors derived from the tumor-inducing (Ti) plasmid of *Agrobacterium tumefaciens* described (Rogers et al., 1987). However, several other plant integrating vector systems are known to function in plants including pCaMVCN transfer control vector described (Fromm et al., 1985). Plasmid pCaMVCN (available from Pharmacia, Piscataway, N.J.) includes the cauliflower mosaic virus CaMV 35S promoter.

In preferred embodiments, the vector used to express the polypeptide includes a selection marker that is effective in a plant cell, preferably a drug resistance selection marker. One preferred drug resistance marker is the gene whose expression results in kanamycin resistance; i.e., the chimeric gene containing the nopaline synthase promoter, Tn5 neomycin phosphotransferase II (nptII) and nopaline synthase 3' non-translated region described (Rogers et al., 1988). Another preferred selection marker is the bar gene, which confers glyphosphate resistance. Selectable markers useful in plant transformation are disclosed in U.S. patent application Ser. No. 08/113,561, filed Aug. 25, 1993, which is specifically incorporated herein by reference.

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

Means for preparing expression vectors are well known in the art. Expression (transformation vectors) used to transform plants and methods of making those vectors are described in U.S. Pat. Nos. 4,971,908, 4,940,835, 4,769,061 and 4,757,011, the disclosures of which are incorporated herein by reference. Those vectors can be modified to include a coding sequence in accordance with the present invention.

A variety of methods have been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

A coding region that encodes a polypeptide having the ability to confer increased levels of benzoxazinone biosynthesis to a cell is preferably a maize Bx1 gene. In preferred embodiments, such a polypeptide has the amino acid residue sequence of SEQ ID NO:2 or a functional equivalent of that sequence.

In other embodiments a Bx gene of the current invention may be operable linked to a transit peptide. In a particular embodiment, this transit peptide may be directed to the chloroplast. The transit peptide may, for example, be a heterologous transit peptide such as that of the small subunit of ribulose bisphosphate carboxylase. In still other embodiments of the current invention, a transit peptide operable linked to a Bx gene may be directed to locations within a plant cell other than the chloroplast.

XIII. Transgenic Bx Plants and Plant Cells

The present invention provides methods for producing a transgenic plant which expresses a nucleic acid segment encoding the Bx1 gene of the present invention. The process of producing transgenic plants is well-known in the art. In general, the method comprises transforming a suitable host cell with a DNA segment which contains a promoter operatively linked to a coding region that encodes a Bx1 gene. Such a coding region is generally operatively linked to a transcription-terminating region, whereby the promoter is capable of driving the transcription of the coding region in the cell, and hence providing the cell the ability to produce the recombinant protein in vivo. Alternatively, in instances where it is desirable to control, regulate, or decrease the amount of a particular recombinant protein expressed in a particular transgenic cell, the invention also provides for the expression of Bx1 protein antisense mRNA. The use of antisense mRNA as a means of controlling or decreasing the amount of a given protein of interest in a cell is well-known in the art.

Another aspect of the invention comprises transgenic plants which express a gene or gene segment encoding one or more of the novel polypeptide compositions disclosed herein. As used herein, the term "transgenic plant" is intended to refer to a plant that has incorporated DNA sequences, which are in addition to those originally present, DNA sequences not normally transcribed into RNA or translated into a protein ("expressed"), or any other genes or DNA sequences which one desires to introduce into the non-transformed plant, such as genes which may normally be present in the non-transformed plant but which one desires to either genetically engineer or to have altered expression.

It is contemplated that in some instances the genome of a transgenic plant of the present invention will have been augmented through the stable introduction of one or more benzoxazinone biosynthesis genes, either native, synthetically modified, or mutated. In some instances, more than one transgene will be incorporated into the genome of the transformed host plant cell. Such is the case when more than one benzoxazinone biosynthesis protein-encoding DNA segment is incorporated into the genome of such a plant. In certain situations, it may be desirable to have one, two, three, four, five or even more benzoxazinone biosynthesis proteins (either native or recombinantly-engineered) incorporated and stably expressed in the transformed transgenic plant.

A preferred gene which may be introduced includes, for example, the maize Bx1 gene. Other preferred genes include Bx2, Bx3, Bx4, Bx5, anthranilate synthase, and ribosyl transferase. Still other preferred genes are those which, when introduced into a plant or plant cell, result in increased biosynthesis of benzoxazinones, thereby increasing the plant or plant cells resistance to particular pathogens, insects, herbicides or other deleterious agents. In a particular embodiment, it may be desired to specifically engineer the gene, in order to enhance the genes efficacy in a particular genetic background for increasing benzoxazinone biosynthesis. This may include creating plants which have an exogenous Bx1 gene in combination with one or more other benzoxazinone biosynthesis genes including Bx2, Bx3, Bx4 and Bx5.

Means for transforming a plant cell and the preparation of a transgenic cell line are well-known in the art, and are discussed herein. Vectors, plasmids, cosmids, YACs (yeast artificial chromosomes) and DNA segments for use in transforming such cells will, of course, generally comprise either the operons, genes, or gene-derived sequences of the present invention, either native, or synthetically-derived, and particularly those encoding the disclosed crystal proteins. These DNA constructs can further include structures such as promoters, enhancers, polylinkers, or even gene sequences which have positively- or negatively-regulating activity upon the particular genes of interest as desired. The DNA segment or gene may encode either a native or modified crystal protein, which will be expressed in the resultant recombinant cells, and/or which will impart an improved phenotype to the regenerated plant.

Such transgenic plants may be desirable for increasing the insecticidal resistance of a monocotyledonous or dicotyledonous plant, by incorporating into such a plant, a transgenic DNA segment encoding one or more benzoxazinone biosynthesis genes. Particularly preferred plants include rye, wheat, maize, and the like.

In a related aspect, the present invention also encompasses a seed produced by the transformed plant, a progeny from such seed, and seed produced by the progeny of the original transgenic plant, produced in accordance with the above process. Such progeny and seeds will have a benzoxazinone biosynthesis protein-encoding transgene stably incorporated into their genome, and such progeny plants will inherit the traits afforded by the introduction of a stable transgene in Mendelian fashion. All such transgenic plants having incorporated into their genome transgenic DNA segments encoding one or more benzoxazinone biosynthesis proteins or polypeptides are aspects of this invention.

(i) Transformed Host Cells and Transgenic Plants

Methods and compositions for transforming a bacterium, a yeast cell, a plant cell, or an entire plant with one or more expression vectors comprising a benzoxazinone biosynthesis protein-encoding gene segment are further aspects of this disclosure. A transgenic bacterium, yeast cell, plant cell or plant derived from such a transformation process or the progeny and seeds from such a transgenic plant are also further embodiments of the invention.

Means for transforming bacteria and yeast cells are well known in the art. Typically, means of transformation are similar to those well known means used to transform other bacteria or yeast such as *E. coli* or *Saccharomyces cerevisiae*. Methods for DNA transformation of plant cells include Agrobacterium-mediated plant transformation, protoplast transformation, gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known which methods are useful for a particular plant strain.

There are many methods for introducing transforming DNA segments into cells, but not all are suitable for delivering DNA to plant cells. Suitable methods are believed to include virtually any method by which DNA can be introduced into a cell, such as by Agrobacterium infection, direct delivery of DNA such as, for example, by PEG-mediated transformation of protoplasts (Omirulleh et al., 1993), by desiccation/inhibition-mediated DNA uptake, by electroporation, by agitation with silicon carbide fibers, by acceleration of DNA coated particles (U.S. Pat. No. 5,550,318), etc. In certain embodiments, acceleration methods are preferred and include, for example, microprojectile bombardment and the like.

Technology for introduction of DNA into cells is well-known to those of skill in the art. Four general methods for delivering a gene into cells have been described: (1) chemical methods (Graham et al., 1973; Zatloukal et al., 1992); (2) physical methods such as microinjection (Capecchi, 1980), electroporation (Wong et al., 1982; Fromm et al., 1985; U.S. Pat. No. 5,384,253) and the gene gun (Johnston et al., 1994; Fynan et al., 1993); (3) viral vectors (Clapp, 1993; Lu et al., 1993; Eglitis et al., 1988a; 1988b); and (4) receptor-mediated mechanisms (Curiel et al., 1991; 1992; Wagner et al., 1992).

(ii) Sources of Cells

Practicing the present invention includes the generation and use of recipient cells. As used herein, the term "recipient cells" refers to cells that are receptive to transformation and subsequent regeneration into stably transformed, fertile plants. Maize recipient cell targets include, but are not limited to, meristem cells, Type I, Type II, and Type III callus, immature embryos and gametic cells such as microspores pollen, sperm and egg cells. Type I, Type II, and Type III callus may be initiated from tissue sources including, but not limited to, immature embryos, seedling apical meristems, microspores and the such. Those cells which are capable of proliferating as callus are also recipient cells for genetic transformation. Pollen, as well as its precursor cells, microspores, may be capable of functioning as recipient cells for genetic transformation, or as vectors to carry foreign DNA for incorporation during fertilization. Direct pollen transformation would obviate the need for cell culture. Meristematic cells (i.e., plant cells capable of continual cell division and characterized by an undifferentiated cytological appearance, normally found at growing points or tissues in plants such as root tips, stem apices, lateral buds, etc.) may represent another type of recipient plant cell. Because of their undifferentiated growth and capacity for organ differentiation and totipotency, a single transformed meristematic cell could be recovered as a whole transformed plant. In fact, it is proposed that embryogenic suspension cultures may be an in vitro meristematic cell system, retaining an ability for continued cell division in an undifferentiated state, controlled by the media environment.

In certain embodiments, cultured plant cells that can serve as recipient cells for transforming with desired DNA segments include corn cells, and more specifically, cells from *Zea mays L.* Somatic cells are of various types. Embryogenic cells are one example of somatic cells which may be induced to regenerate a plant through embryo formation. Non-embryogenic cells are those which will typically not respond in such a fashion. An example of non-embryogenic cells are certain Black Mexican Sweet (BMS) corn cells.

The development of embryogenic maize calli and suspension cultures useful in the context of the present invention, e.g., as recipient cells for transformation, has been described in U.S. Ser. No. 06/877,033, filed Jun. 07, 1986 incorporated herein by reference.

The present invention also provides certain techniques that may enrich recipient cells within a cell population. For example, Type II callus development, followed by manual selection and culture of friable, embryogenic tissue, generally results in an enrichment of recipient cells for use in, e.g., micro-projectile transformation. Suspension culturing, particularly using the media disclosed herein, may also improve the ratio of recipient to non-recipient cells in any given population. Manual selection techniques which are employed to select recipient cells may include, e.g., assessing cell morphology and differentiation, or may use various physical or biological means. Cryopreservation is also contemplated as a possible method of selecting for recipient cells.

Manual selection of recipient cells, e.g., by selecting embryogenic cells from the surface of a Type II callus, is one means employed by the inventors in an attempt to enrich for recipient cells prior to culturing (whether cultured on solid media or in suspension). The preferred cells may be those located at the surface of a cell cluster, and may further be identifiable by their lack of differentiation, their size and dense cytoplasm. The preferred cells will generally be those cells which are less differentiated, or not yet committed to differentiation. Thus, one may wish to identify and select those cells which are cytoplasmically dense, relatively unvacuolated with a high nucleus to cytoplasm ratio (e.g., determined by cytological observations), small in size (e.g., 10–20 mm), and capable of sustained divisions and somatic proembryo formation.

It is proposed that other means for identifying such cells may also be employed. For example, through the use of dyes, such as Evan's blue, which are excluded by cells with relatively non-permeable membranes, such as embryogenic cells, and taken up by relatively differentiated cells such as root-like cells and snake cells (so-called due to their snake-like appearance).

Other possible means of identifying recipient cells include the use of isozyme markers of embryogenic cells, such as glutamate dehydrogenase, which can be detected by cytochemical stains (Fransz et al., 1989). However, it is cautioned that the use of isozyme markers such as glutamate dehydrogenase may lead to some degree of false positives from non-embryogenic cells such as rooty cells which nonetheless have a relatively high metabolic activity.

(iii) Media

In certain embodiments, recipient cells are selected following growth in culture. Where employed, cultured cells will preferably be grown either on solid supports or in the form of liquid suspensions. In either instance, nutrients may be provided to the cells in the form of media, and environmental conditions controlled. There are many types of tissue culture media comprised of amino acids, salts, sugars, growth regulators and vitamins. Most of the media employed in the practice of the invention will have some similar components, the media differ in the composition and proportions of their ingredients depending on the particular application envisioned. For example, various cell types usually grow in more than one type of media, but will exhibit different growth rates and different morphologies, depending on the growth media. In some media, cells survive but do not divide.

Various types of media suitable for culture of plant cells have been previously described. Examples of these media include, but are not limited to, the N6 medium described by Chu et al. (1975) and MS media (Murashige & Skoog, 1962). The inventors have discovered that media such as MS which have a high ammonia/nitrate ratio are counterproductive to the generation of recipient cells in that they promote loss of morphogenic capacity. N6 media, on the other hand, has a somewhat lower ammonia/nitrate ratio, and is contemplated to promote the generation of recipient cells by maintaining cells in a proembryonic state capable of sustained divisions.

(iv) Cell Cultures

1. Initiation

In the practice of the invention it is sometimes, but not always, necessary to develop cultures which contain recipient cells. Suitable cultures can be initiated from a number of whole plant tissue explants including, but not limited to, immature embryos, leaf bases, immature tassels, anthers, microspores, and other tissues containing cells capable of in vitro proliferation and regeneration of fertile plants. In one exemplary embodiment, recipient cell cultures are initiated from immature embryos of *Zea mays L.* by growing excised immature embryos on a solid culture medium containing growth regulators including, but not limited to, dicamba., 2,4-D, NAA, and IAA. In some instances it will be preferred to add silver nitrate to culture medium for callus initiation as this compound has been reported to enhance culture initiation (Vain et al., 1989). Embryos will produce callus that varies greatly in morphology including from highly unorganized cultures containing very early embryogenic structures (such as, but not limited to, type II cultures in maize), to highly organized cultures containing large late embryogenic structures (such as, but not limited to, type I cultures in maize). This variation in culture morphology may be related to genotype, culture medium composition, size of the initial embryos and other factors. Each of these types of culture morphologies is a source of recipient cells.

The development of suspension cultures capable of plant regeneration may be used in the context of the present invention. Suspension cultures may be initiated by transferring callus tissue to liquid culture medium containing growth regulators. Addition of coconut water or other substances to suspension culture medium may enhance growth and culture morphology, but the utility of suspension cultures is not limited to those containing these compounds. In some embodiments of this invention, the use of suspension cultures will be preferred as these cultures grow more rapidly and are more easily manipulated than callus cells growing on solid culture medium.

When immature embryos or other tissues directly removed from a whole plant are used as the target tissue for DNA delivery, it will only be necessary to initiate cultures of cells insofar as is necessary for identification and isolation of transformants. In an illustrative embodiment, DNA is introduced by particle bombardment into immature embryos following their excision from the plant. Embryos are transferred to a culture medium that will support proliferation of tissues and allow for selection of transformed sectors, 0–14 days following DNA delivery. In this embodiment of the invention it is not necessary to establish stable callus cultures capable of long term maintenance and plant regeneration.

2. Maintenance

The method of maintenance of cell cultures may contribute to their utility as sources of recipient cells for transformation. Manual selection of cells for transfer to fresh culture medium, frequency of transfer to fresh culture medium, composition of culture medium, and environment factors including, but not limited to, light quality and quantity and temperature are all important factors in maintaining callus and/or suspension cultures that are useful as sources of recipient cells. It is contemplated that alternating callus between different culture conditions may be beneficial in enriching for recipient cells within a culture. For example, it is proposed that cells may be cultured in suspension culture, but transferred to solid medium at regular intervals. After a period of growth on solid medium cells can be manually selected for return to liquid culture medium. It is proposed that by repeating this sequence of transfers to fresh culture medium it is possible to enrich for recipient cells. It is also contemplated that passing cell cultures through a 1.9 mm sieve is useful in maintaining the friability of a callus or suspension culture and may be beneficial is enriching for transformable cells.

3 Cryopreservation

Additionally, the inventors propose that cryopreservation may effect the development of, or perhaps select for, recipient cells. Cryopreservation selection may operate due to a selection against highly vacuolated, non-embryogenic cells, which may be selectively killed during cryopreservation. The inventors propose that there is a temporal window in which cultured cells retain their regenerative ability, thus, it is believed that they must be preserved at or before that temporal period if they are to be used for future transformation and regeneration.

For use in transformation, suspension or callus culture cells may be cryopreserved and stored for periods of time, thawed, then used as recipient cells for transformation. An illustrative embodiment of cryopreservation methods comprises the steps of slowly adding cryoprotectants to suspension cultures to give a final concentration of 10% dimethyl sulfoxide, 10% polyethylene glycol (6000 MW), 0.23 M proline and 0.23 M glucose. The mixture is then cooled to −35° C. at 0.5° C. per minute. After an isothermal period of 45 minutes, samples are placed in liquid $N_2$ (modification of methods of Withers and King (1979); and Finkle et al. (1985)). To reinitiate suspension cultures from cryopreserved material, cells may be thawed rapidly and pipetted onto feeder plates similar to those described by Rhodes et al. (Vaeck et al., 1987).

XIV. DNA Sequences

Virtually any DNA composition may be used for delivery to recipient cells by modem transformation techniques to ultimately produce fertile transgenic plants. In accordance with the present invention the genes used to create transgenic plants will be Bx genes of DIMBOA biosynthesis. By way of example, DNA segments in the form of vectors and plasmids, or linear DNA fragments, in some instances containing only the Bx gene DNA element to be expressed in the plant, and the like, may be employed.

In certain embodiments, it is contemplated that one may wish to employ replication-competent viral vectors in monocot transformation. Such vectors include, for example, wheat dwarf virus (WDV) "shuttle" vectors, such as pW1-11 and PW1-GUS (Ugaki et al., 1991). These vectors are capable of autonomous replication in maize cells as well as E. coli, and as such may provide increased sensitivity for detecting DNA delivered to transgenic cells. A replicating vector may also be useful for delivery of genes flanked by DNA sequences from transposable elements such as Ac, Ds, or Mu. It has been proposed (Laufs et al., 1990) that transposition of these elements within the maize genome requires DNA replication. It is also contemplated that transposable elements would be useful for introducing DNA fragments lacking elements necessary for selection and maintenance of the plasmid vector in bacteria, e.g., antibiotic resistance genes and origins of DNA replication. It is also proposed that use of a transposable element such as Ac, Ds, or Mu would actively promote integration of the desired DNA and hence increase the frequency of stably transformed cells.

Vectors, plasmids, cosmids, YACs (yeast artificial chromosomes) and DNA segments for use in transforming such cells will, of course, generally comprise the cDNA, gene or genes which one desires to introduce into the cells. These DNA constructs can further include structures such as promoters, enhancers, polylinkers, or even regulatory genes as desired. The DNA segment or gene chosen for cellular introduction will encode a protein involved in bezoxazinone biosynthesis and will be expressed in the resultant recombinant cells, such as will result in a screenable or selectable trait and/or which will impart an improved phenotype to the regenerated plant.

(i) Regulatory Elements

The construction of vectors which may be employed in conjunction with the present invention will be known to those of skill of the art in light of the present disclosure (see e.g., Sambrook et al., 1989; Gelvin et al., 1990). Preferred constructs will generally include a plant promoter such as the CaMV 35S promoter (Odell et al., 1985), or others such as CaMV 19S (Lawton et al., 1987), nos (Ebert et al., 1987), Adh (Walker et al., 1987), sucrose synthase (Yang & Russell, 1990), a-tubulin, actin (Wang et al., 1992), cab (Sullivan et al., 1989), PEPCase (Hudspeth & Grula, 1989) or those associated with the R gene complex (Chandler et al., 1989). Tissue specific promoters such as root cell promoters (Conkling et al., 1990) and tissue specific enhancers (Fromm et al., 1989) are also contemplated to be particularly useful, as are inducible promoters such as ABA- and turgor-inducible prompters.

Constructs will also include the gene of interest along with a 3' end DNA sequence that acts as a signal to terminate transcription and allow for the poly-adenylation of the resultant mRNA. The most preferred 3' elements are contemplated to be those from the nopaline synthase gene of *Agrobacterium tumefaciens* (Bevan et al., 1983), the terminator for the T7 transcript from the octopine synthase gene of *Agrobacterium tumefaciens,* and the 3' end of the protease inhibitor I or II genes from potato or tomato. Regulatory elements such as Adh intron 1 (Callis et al., 1987), sucrose synthase intron (Vasil et al., 1989) or TMV omega element (Gallie, et al., 1989), or actin intron (Wang et al., 1992), may further be included where desired.

As the DNA sequence between the transcription initiation site and the start of the coding sequence, i.e., the untranslated leader sequence, can influence gene expression, one may also wish to employ a particular leader sequence. Preferred leader sequences are contemplated to include those which include sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants, and in maize in particular, will be most preferred.

It is contemplated that vectors for use in accordance with the present invention may be constructed to include the ocs enhancer element. This element was first identified as a 16 bp palindromic enhancer from the octopine synthase (ocs) gene of Agrobacterium (Ellis et al., 1987), and is present in at least 10 other promoters (Bouchez et al., 1989). It is proposed that the use of an enhancer element, such as the ocs element and particularly multiple copies of the element, will act to increase the level of transcription from adjacent promoters when applied in the context of monocot transformation.

It is specifically envisioned that Bx genes may be introduced under the control of novel promoters or enhancers, etc., or perhaps even homologous or tissue specific (e.g., root-, collar/sheath-, whorl-, stalk-, earshank-, kernel- or leaf-specific) promoters or control elements. Indeed, it is envisioned that a particular use of the present invention will be the targeting of benzoxazinone biosynthesis in a tissue-specific manner. For example, insect resistant genes may be expressed specifically in the whorl and collar/sheath tissues which are targets for the first and second broods, respectively, of ECB. Likewise, activity against rootworm may be targeted by directly enhancing bezoxazinone biosynthesis in root tissues.

Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue; a truncated (−90 to +8) 35S promoter which directs enhanced expression in roots, an a-tubulin gene that directs expression in roots and promoters derived from zein storage protein genes which direct expression in endosperm. It is particularly contemplated that one may advantageously use the 16 bp ocs enhancer element from the octopine synthase (ocs) gene (Ellis et al., 1987; Bonchez et al., 1989), especially when present in multiple copies, to achieve enhanced expression in roots.

It is also contemplated that tissue specific expression may be functionally accomplished by introducing a constitutively expressed gene (all tissues) in combination with an antisense gene that is expressed only in those tissues where the gene product is not desired. For example, a gene coding for a Bx gene may be introduced such that it is expressed in all tissues using the 35S promoter from Cauliflower Mosaic Virus. Expression of an antisense transcript of the same Bx gene in a maize kernel, using for example a zein promoter, would prevent accumulation of benzoxazinones in seed. Hence bezoxazinones may be synthesized in all tissues except the kernel.

Alternatively, one may wish to obtain novel tissue-specific promoter sequences for use in accordance with the present invention. To achieve this, one may first isolate cDNA clones from the tissue concerned and identify those clones which are expressed specifically in that tissue, for example, using Northern blotting. Ideally, one would like to identify a gene that is not present in a high copy number, but which gene product is relatively abundant in specific tissues. The promoter and control elements of corresponding genomic clones may then be localized using the techniques of molecular biology known to those of skill in the art.

It is contemplated that expression of Bx genes in transgenic plants may in some cases be desired only under specified conditions. It is contemplated that expression of such genes at high levels may have detrimental effects. It is known that a large number of genes exist that respond to the environment. For example, expression of some genes such as rbcS, encoding the small subunit of ribulose bisphosphate carboxylase, is regulated by light as mediated through phytochrome. Other genes are induced by secondary stimuli. A number of genes have been shown to be induced by ABA (Skriver and Mundy, 1990). It is also anticipated that expression of Bx genes may be desired only under conditions of actual insect infestation. Therefore, in particular embodiments, inducible expression of Bx genes in transgenic plants may be desired.

It is proposed that in some embodiments of the present invention expression of a Bx gene in a transgenic plant will be desired only in a certain time period during the development of the plant. Developmental timing is frequently correlated with tissue specific gene expression. For example, expression of zein storage proteins is initiated in the endosperm about 15 days after pollination.

Additionally, vectors may be constructed and employed in the intracellular targeting of a specific gene product within the cells of a transgenic plant or in directing a protein to the extracellular environment. This will generally be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed. Transit or signal peptides act by facilitating the transport of proteins through intracellular membranes, e.g., vacuole, vesicle, plastid and mitochondrial membranes, whereas signal peptides direct proteins through the extracellular membrane.

A particular example of such a use concerns the direction of a herbicide resistance gene, such as the EPSPS gene, to a particular organelle such as the chloroplast rather than to the cytoplasm. This is exemplified by the use of the rbcS transit peptide which confers plastid-specific targeting of proteins. In addition, it is proposed that it may be desirable to target Bx genes to the extracellular spaces or to the vacuole.

It is also contemplated that it may be useful to target DNA itself within a cell. For example, it may be useful to target introduced DNA to the nucleus as this may increase the frequency of transformation. Within the nucleus itself it would be useful to target a gene in order to achieve site specific integration. For example, it would be useful to have an gene introduced through transformation replace an existing gene in the cell.

(ii) Marker Genes

In order to improve the ability to identify transformants, one may desire to employ a selectable or screenable marker gene as, or in addition to, the expressible gene of interest. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., a-amylase, b-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

One example of a protein suitable for modification in this manner is extensin, or hydroxyproline rich glycoprotein (HPRG). The use of the maize HPRG (Steifel et al., 1990) which is preferred as this molecule is well characterized in terms of molecular biology, expression and protein structure. However, any one of a variety of extensins and/or glycine-rich wall proteins (Keller et al., 1989) could be modified by the addition of an antigenic site to create a screenable marker.

One exemplary embodiment of a secretable screenable marker concerns the use of the maize genomic clone encoding the wall protein HPRG, modified to include the unique 15 residue epitope M A T V P E L N C E M P P S D from the pro-region of murine interleukin-1-β (IL-1-β). However, virtually any detectable epitope may be employed in such embodiments, as selected from the extremely wide variety of antigen:antibody combinations known to those of skill in the art. The unique extracellular epitope, whether derived from IL-1-β or any other protein or epitopic substance, can then be straightforwardly detected using antibody labeling in conjunction with chromogenic or fluorescent adjuncts.

Elements of the present disclosure are exemplified in detail through the use of the bar and/or GUS genes, and also through the use of various other markers. Of course, in light of this disclosure, numerous other possible selectable and/or screenable marker genes will be apparent to those of skill in the art in addition to the one set forth hereinbelow. Therefore, it will be understood that the following discussion is exemplary rather than exhaustive. In light of the techniques disclosed herein and the general recombinant techniques which are known in the art, the present invention renders possible the introduction of any gene, including marker genes, into a recipient cell to generate a transformed plant.

(iii) Selectable Markers

Possible selectable markers for use in connection with the present invention include, but are not limited to, a neo gene (Potrykus et al., 1985) which codes for kanamycin resistance and can be selected for using kanamycin, G418, etc.; a bar gene which codes for bialaphos resistance; a mutant gene which encodes an altered EPSP synthase protein (Hinchee et al., 1988) thus conferring glyphosate resistance; a nitrilase gene such as bxn from *Klebsiella ozaenae* which confers resistance to bromoxynil (Stalker et al., 1988); a mutant acetolactate synthase gene (ALS) which confers resistance to imidazolinone, sulfonylurea or other ALS inhibiting chemicals (European Patent Application 154,204, 1985); a methotrexate resistant DHFR gene (Thillet et al., 1988), or a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (European Pat. No. 0189707).

An illustrative embodiment of a selectable marker gene capable of being used in systems to select transformants is the genes that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

Where one desires to employ a bialaphos resistance gene in the practice of the invention, the inventors have discovered that a particularly useful gene for this purpose is the bar or pat genes obtainable from species of Streptomyces (e.g., ATCC No. 21,705). The cloning of the bar gene has been described (Murakami et al., 1986; Thompson et al., 1987) as has the use of the bar gene in the context of plants other than monocots (De Block et al., 1987; De Block et al., 1989).

(iv) Screenable Markers

Screenable markers that may be employed include a β-glucuronidase or uidA gene (GUS) which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an a-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; a green fluorescent protein (GFP) gene, or even an aequorin gene (Prasher et al., 1985), which may be employed in calcium-sensitive bioluminescence detection.

Genes from the maize R gene complex are contemplated to be particularly useful as screenable markers. The R gene complex in maize encodes a protein that acts to regulate the production of anthocyanin pigments in most seed and plant tissue. Maize strains can have one, or as many as four, R alleles which combine to regulate pigmentation in a developmental and tissue specific manner. The R gene complex in transformed cells does not harm the cells. Thus, an R gene introduced into such cells will cause the expression of a red pigment and, if stably incorporated, can be visually scored as a red sector. If a maize line carries dominant alleles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 which contains the rg-Stadler allele and TR112, a K55 derivative which is r-g, b, P1. Alternatively any genotype of maize can be utilized if the C1 and R alleles are introduced together.

The inventors further propose that R gene regulatory regions may be employed in chimeric constructs in order to provide mechanisms for controlling the expression of chimeric genes. More diversity of phenotypic expression is known at the R locus than at any other locus (Coe et al., 1988). It is contemplated that regulatory regions obtained from regions 5' to the structural R gene would be valuable in directing the expression of genes for, e.g., insect resistance, herbicide tolerance or other protein coding regions. For the purposes of the present invention, it is believed that any of the various R gene family members may be successfully employed (e.g., P, S, Lc, etc.). However, the most preferred will generally be Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for populational screening for bioluminescence, such as on tissue culture plates, or even for whole plant screening.

It is further contemplated that a gene encoding green fluorescent protein (GFP) could also be used as a screenable marker. Cells expressing GFP fluoresce when illuminated with light of particular wavelengths, especially ultraviolet light. Cells or plants expressing GFP can thereby be readily identified.

(v) Negative Selectable Markers

It is contemplated that in particular embodiments a negative selectable marker may be used with the current invention. It is contemplated that when two or more genes are introduced together by cotransformation that the genes will be linked together on the host chromosome. For example, a gene encoding a Bx protein that confers insect resistance on the plant may be introduced into a plant together with a bar gene that is useful as a selectable marker and confers resistance to the herbicide Ignite® on the plant. However, it may not be desirable to have an insect resistant plant that is also resistant to the herbicide Ignite®. It is proposed that one could also introduce an antisense bar gene that is expressed in those tissues where one does not want expression of the bar gene, e.g., in whole plant parts. Hence, although the bar gene is expressed and is useful as a selectable marker, it is not useful to confer herbicide resistance on the whole plant. The bar antisense gene is a negative selectable marker.

It is also contemplated that a negative selection is necessary in order to screen a population of transformants for rare homologous recombinants generated through gene targeting. For example, a homologous recombinant may be identified through the inactivation of a gene that was previously expressed in that cell. The antisense gene to neomycin phosphotransferase II (nptII) has been investigated as a negative selectable marker in tobacco (*Nicotiana tabacum*) and *Arabidopsis thaliana* (Xiang, C. and Guerra, D. J. 1993). In this example both sense and antisense npt II genes are introduced into a plant through transformation and the resultant plants are sensitive to the antibiotic kanamycin. An introduced gene that integrates into the host cell chromosome at the site of the antisense nptII gene, and inactivates the antisense gene, will make the plant resistant to kanamycin and other aminoglycoside antibiotics. Therefore, rare site specific recombinants may be identified by screening for antibiotic resistance. Similarly, any gene, native to the plant or introduced through transformation, that when inactivated confers resistance to a compound, may be useful as a negative selectable marker.

XV. Transformation Techniques

Potentially any method capable of for transforming DNA segments into cells could be used to introduce an exogenous benzoxazinone biosynthesis gene, but not all are suitable for delivering DNA to plant cells. Suitable methods are believed to include virtually any method by which DNA can be introduced into a cell, such as by Agrobacterium infection (described in, for example, U.S. Pat. No. 5,591,616, specifically incorporated herein by reference in its entirety); direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253), by agitation with silicon carbide fibers (Kaeppler et al. 1990), and by acceleration of DNA coated particles (U.S. Pat. No. 5,550,318), etc. Through the application of techniques such as these, certain cells from virtually any plant species may be stably transformed, and these cells developed into transgenic plants. In certain embodiments, acceleration methods are preferred and include, for example, microprojectile bombardment and the like.

(i) Electroporation

The application of brief, high-voltage electric pulses to a variety of bacterial, animal and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

The introduction of DNA by means of electroporation, is well-known to those of skill in the art. In this method, certain cell wall-degrading enzymes, such as pectin-degrading enzymes, are employed to render the target recipient cells more susceptible to transformation by electroporation than untreated cells. Alternatively, recipient cells are made more susceptible to transformation, by mechanical wounding. To effect transformation by electroporation one may employ either friable tissues such as a suspension culture of cells, or embryogenic callus, or alternatively, one may transform immature embryos or other organized tissues directly. One would partially degrade the cell walls of the chosen cells by exposing them to pectin-degrading enzymes (pectolyases) or mechanically wounding in a controlled manner. Such cells would then be recipient to DNA transfer by electroporation, which may be carried out at this stage, and transformed cells then identified by a suitable selection or screening protocol dependent on the nature of the newly incorporated DNA.

(ii) Microprojectile Bombardment

A further advantageous method for delivering transforming DNA segments to plant cells is microprojectile bombardment. In this method, particles may be coated with nucleic acids and delivered into cells by a propelling force. Exemplary particles include those comprised of tungsten, gold, platinum, and the like.

An advantage of microprojectile bombardment, in addition to it being an effective means of reproducibly stably transforming monocots, is that neither the isolation of protoplasts (Christou et al., 1988) nor the susceptibility to Agrobacterium infection is required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with corn cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing damage inflicted on the recipient cells by projectiles that are too large.

For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from 1 to 10 and average 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

(iii) Agrobacterium-Mediated Transfer

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described (Fraley et al., 1985; Rogers et al., 1987). Further, the integration of the Ti-DNA is a relatively precise process resulting in few rearrangements. The region of DNA to be transferred is defined by the border sequences, and intervening DNA is usually inserted into the plant genome as described (Spielmann et al., 1986; Jorgensen et al., 1987).

Modern Agrobacterium transformation vectors are capable of replication in E. coli as well as Agrobacterium, allowing for convenient manipulations as described (Klee et al., 1985). Moreover, recent technological advances in vectors for Agrobacterium-mediated gene transfer have improved the arrangement of genes and restriction sites in the vectors to facilitate construction of vectors capable of expressing various polypeptide coding genes. The vectors described (Rogers et al., 1987), have convenient multi-linker regions flanked by a promoter and a polyadenylation site for direct expression of inserted polypeptide coding genes and are suitable for present purposes. In addition, Agrobacterium containing both armed and disarmed Ti genes can be used for the transformations. In those plant strains where Agrobacterium-mediated transformation is efficient, it is the method of choice because of the facile and defined nature of the gene transfer.

Agrobacterium-mediated transformation of leaf disks and other tissues such as cotyledons and hypocotyls appears to be limited to plants that Agrobacterium naturally infects. Agrobacterium-mediated transformation is most efficient in dicotyledonous plants. Few monocots appear to be natural hosts for Agrobacterium, although transgenic plants have been produced in asparagus using Agrobacterium vectors as described (Bytebier et al., 1987). Therefore, commercially important cereal grains such as rice, corn, and wheat must usually be transformed using alternative methods. Agrobacterium-mediated transformation of maize has, however, recently been described in U.S. Pat. No. 5,591,616, which is specifically incorporated herein by reference. Further, it has been shown that homozygous bx mutants are more susceptible to Agrobacterium-mediated transformation.

A transgenic plant formed using Agrobacterium transformation methods typically contains a single transgene or a few copies of a transgene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant is hemizygous.

More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) a hemizygous transgenic plant that contains a single added gene, germinating some of the seed produced and analyzing the resulting plants produced for enhanced carboxylase activity relative to a control (native, non-transgenic) or a hemizygous transgenic plant.

It is to be understood that two different transgenic plants can also be mated to produce offspring that contain multiple independently segregating added, exogenous genes. Specifically contemplated by the inventors, is the creation of plants which contain 1,2,3,4,5, or even more independently segregating added, exogenous genes. Selfing of appropriate progeny can produce plants that are homozygous for all added, exogenous genes that encode a polypeptide of interest. Back-crossing to a parental plant and out-crossing with a non-transgenic plant are also contemplated.

(iv) Other Transformation Methods

Transformation of plant protoplasts can be achieved using methods based on calcium phosphate precipitation, polyethylene glycol treatment, electroporation, and combinations of these treatments (see, e.g., Potrykus et al., 1985; Lorz et al., 1985; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts are described (Fujimura et al., 1985; Toriyama et al., 1986; Yamada et al., 1986; Abdullah et al., 1986).

To transform plant strains that cannot be successfully regenerated from protoplasts, other ways to introduce DNA into intact cells or tissues can be utilized. For example, regeneration of cereals from immature embryos or explants can be effected as described (Vasil, 1988). In addition, "particle gun" or high-velocity microprojectile technology can be utilized (Vasil, 1992).

Using that latter technology, DNA is carried through the cell wall and into the cytoplasm on the surface of small metal particles as described (Klein et al., 1987; Klein et al., 1988; McCabe et al., 1988). The metal particles penetrate through several layers of cells and thus allow the transformation of cells within tissue explants.

XVI. Methods for Producing Plants Resistant to Various Pathogens and Chemical Agents By transforming a suitable host cell, such as a plant cell, with a recombinant Bx1 gene-containing segment, expression of the encoded Bx1 gene (i.e., a protein catalyzing DIMBOA biosynthesis) can result in the formation of plants with enhanced expression of benzoxazinones, which cells thereby have increased resistance to various insects, pathogens and chemical agents. Additionally, it may be desired for the Bx1 gene to be transformed in combinations with one or more other benzoxazinone biosynthesis genes such as Bx2, Bx3, Bx4 and Bx5. All possible combinations of Bx1 with Bx2, Bx3, Bx4 and/or Bx5 are specifically contemplated by the inventors.

It is also contemplated by the inventors that particular combinations of transformed benzoxazinone biosynthesis genes may be created by standard plant breeding methods, which are well known in the art. Such breeding protocols may be aided by the use of genetic markers which are closely linked to the genes of interest.

A preferred method for transformation with Bx genes envisioned by the inventors is microprojectile bombardment. Techniques for microprojectile bombardment are well known in the art, and are described in, for example, Lundquist et al., U.S. Pat. No. 5,538,880 and Adams et al. U.S. Pat. No. 5,489,520, which are specifically incorporated herein by reference.

By way of example, one may utilize an expression vector containing a coding region for a Bx1 gene and an appropriate selectable marker to transform a suspension of embryogenic plant cells, such as wheat or corn cells, using a method such as particle bombardment (Maddock et al., 1991; Vasil et al., 1992) to deliver the DNA coated on microprojectiles into the recipient cells. Transgenic plants are then regenerated from transformed embryogenic calli that express the insecticidal proteins.

The formation of transgenic plants may also be accomplished using other methods of cell transformation which are known in the art such as Agrobacterium-mediated DNA transfer (Fraley et al., 1983). Alternatively, DNA can be introduced into plants by direct DNA transfer into pollen (Zhou et al., 1983; Hess, 1987; Luo et al., 1988), by injection of the DNA into reproductive organs of a plant (Pena et al., 1987), or by direct injection of DNA into the cells of immature embryos followed by the rehydration of desiccated embryos (Neuhaus et al., 1987; Benbrook et al., 1986).

The regeneration, development, and cultivation of plants from single plant protoplast transformants or from various transformed explants is well known in the art (Weissbach et al., 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Protoplast methods of transformation of maize are described in U.S. Pat. No. 5,350,689.

The development or regeneration of plants containing the foreign, exogenous gene that encodes a polypeptide of interest introduced by Agrobacterium from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al., 1983).

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, as discussed before. Otherwise, pollen obtained from the regenerated plants is crossed to seed-grown plants of agronomically important, preferably inbred lines. Conversely, pollen from plants of those important lines is used to pollinate regenerated plants. A transgenic plant of the present invention containing a desired polypeptide is cultivated using methods well known to one skilled in the art.

A transgenic plant of this invention thus has an increased amount of the Bx1 protein, or the Bx1 protein in combination with other benzoxazinone biosynthesis proteins, and thereby, an enhanced level of benzoxazinones such as DIBOA or DIMBOA. A preferred transgenic plant is hemizygous and can transmit particular genes and their activities to its progeny. A more preferred transgenic plant is homozygous for the foreign gene or genes, and transmits the gene or genes to all of its offspring on sexual mating. Seed from a transgenic plant may be grown in the field or greenhouse, and resulting sexually mature transgenic plants are self-pollinated to generate true breeding plants. The progeny from these plants become true breeding lines that are evaluated for, by way of example, increased insecticidal activity or increased resistance to bacterial or fungal disease, preferably in the field, under a range of environmental conditions. The inventors contemplate that the present invention will find particular utility in the creation of transgenic plants of commercial interest including various turf grasses, wheat, corn, rice, barley, oats, a variety of ornamental plants and vegetables, as well as a number of nut- and fruit-bearing trees and plants.

XVII. A Novel Method for the Production of Indole

The present inventors specifically contemplate the use of the gene sequences described herein and the proteins derived from such sequences in the production of indole. In particular, the inventors contemplate the use of the Bx1 protein for the production of free indole from indole-3-glycerol phosphate. In Example 12, it is shown that the Bx1 protein is approximately 30 times more efficient in the production of indole from indole-3-glycerol phosphate than is the native $\alpha_2\beta_2$ enzyme complex which is responsible for this activity in E. coli.

Therefore, the Bx1 protein can be used, either in vivo or ex vivo, for the production of indole, a compound having many uses in industry and food preparation. For example, one could transform a suitable host cell, such as a yeast or bacterial cell, culture transformed cells in growth media, and isolate free indole from the growth media including the transgenic cells. The growth media could be enriched for the substrate indole-3-glycerol phosphate, or alternatively, the substrate may be produced by the endogenous activity of the host cell enzymes. For ex vivo indole production, the Bx1 protein could be produced by a culture of Bx1 transgenic cells, isolated from the culture, and then placed in a reaction mixture containing indole-3-glycerol phosphate, where the Bx1 protein will efficiently catalyze the production of indole.

XVIII. Utilization of Transgenic Crops

The ultimate goal in the production of transgenic plants having enhanced characteristics is to produce plants which are useful to man. In this respect, transgenic plants created in accordance with the current invention may be used for virtually any purpose deemed of value to the grower or to the consumer. For example, one may wish to harvest seed from transgenic plants. This seed may in turn be used for a wide variety of purposes. The seed may be sold to farmers for planting in the field or may be directly used as food, either for animals or humans. Alternatively, products may be made from the seed itself. Examples of products which may be made from the seed include, oil, starch, animal or human food, pharmaceuticals, and various industrial products. Such products may be made from particular plant parts or from the entire plant. One product made from the entire plant, which is deemed of particular value, is silage for animal feed.

Means for preparing products from plants, such as those that may be made with the current invention, have been well known since the dawn of agriculture and will be known to those of skill in the art. Specific methods for crop utilization may be found in, for example, Sprague and Dudley (1988), and Watson and Ramstad (1987).

XIX. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Identification of a Mu Tagged bx1 Allele

To clone the Bx1 gene, a targeted transposon tagging approach was utilized (Chomet et al., 1994). Mu-active female lines were crossed with the pollen from plants homozygous for the recessive bx1 standard mutant allele (Hamilton, 1964) to uncover the integration of a Mu-element in the Bx1 gene. A total of 150 000 F1 seedlings were screened in the root-staining assay of Simcox et al., (1985) and 17 putative integration mutants were identified and outcrossed to an inbred Bx1/Bx1 line. Co-segregation analysis had previously demonstrated that Bx1 and CYP71C1 (Frey et al., 1995) are 6 cM apart. This close linkage was used to determine the presence of the Mu-induced (bx1::Mu) or standard bx1 allele in the progeny. An RFLP was identified that allowed the inventors to distinguish between the CYP71C1 alleles in the Mu tagging population and the bx1 standard line. To facilitate the analysis, a polymorphism between these lines was converted into a CAPS marker. Primers were constructed to CYP71C1 using the published sequence (Genbank Accession X81828). These primers were then used to PCR amplify the corresponding segment from maize genomic DNA. This amplified fragment was digested with the restriction enzyme RsaI, revealing a restriction site polymorphism between the standard bx1 mutant and the Mu tagging population The segregation of the bx1 alleles in the progeny of the crosses was followed using this CAPS marker (Konieczny et al., 1993) derived from the linked Bx4 gene. One of the putative mutants showed the expected 1:1 segregation for the bx1 standard allele and the newly Mu-induced recessive bx1 allele with respect to the linked marker. This mutant was outcrossed with the wild type line H99 and the resulting progeny classified as Bx1, bx1 or Bx1, bx1::Mu according to the CYP71C1 derived CAPS marker. Individual plants of both genotypes were selfed and the homozygous mutants (bx1, bx1 or bx1::Mu, bx1::Mu) in the resulting F2 were determined by the previously described root staining assay.

Due to this pedigree, Mu-elements were present in both types of mutants and most of them segregated independently of the Bx1 gene. The Mu-element integrated in the Bx1 gene, however, was present exclusively and without exception in the Mu-insertion mutants.

The Mu element, which co-segregated with the new bx1::Mu allele, was identified and a flanking genomic DNA fragment was isolated by a polymerase chain reaction (PCR) based method as described in Example 2. This fragment was used to isolate the wildtype Bx1 and the standard recessive bx1 alleles from genomic λ-libraries as well as a full length cDNA clone, isolated from a seedling cDNA library. The sequence of the isolated wildtype Bx1 gene is given in SEQ ID NO:4. The seedling cDNA libraries are commercially available from Stratagene, Inc. DNA sequence analysis revealed that the standard recessive bx1 allele harbored a deletion of 924 bp comprising 355 bp of the 5' non-transcribed region, the first exon, the following intron, and 53 bp of the second exon. The position of the Mu element in the bx1::Mu allele isolated in the transposon tagging experiment, was determined by PCR amplification of the flanking genomic sequences. DNA sequence analysis revealed the exact Mu insertion site and the characteristic 9 bp host sequence duplication associated with integration of the transposon.

Example 2

Identification of Mu-Tagged Sites by Amplification of Insertion Mutagenized Sites (AIMS)

DNA was extracted from individuals of the genotype bx1, bx1 and bx1::Mu, bx1::Mu respectively, and digested either with the restriction endonuclease Bfal or the enzyme Msel. Linker sequences were ligated as described by Vos et al. For the isolation of Mu-element insertion sequences, a linear PCR was performed using a biotinylated primer complementary to the Mu-element ends and the amplification product was separated with streptavidin coated magnetic beads. The isolated sequences were amplified by PCR with Bfal or Msel linker-specific primer and a radioactive labeled nested Mu-specific primer. To lower the complexity of the amplified sequences, the linker-specific primer had a one nucleotide extension at its 3'-end and individual reactions were made for all eight linker primers. The PCR products were analyzed on sequencing gels. Only one band of 180 bp was co-segregating with the bx1::Mu, bx1::Mu genotype in the Bfal digest and an individual band of 291 bp was characteristic for the bx1::Mu, bx1::Mu genotype in the assay made with Msel digested DNA. Plants analyzed included: 10 bx1::Mu, bx1::Mu, 10 bx1,bx1 for Bfal, and 9 bx1::Mu, bx1::Mu 9 bx1, bx1, for Msel, respectively. Both fragments were isolated, sub-cloned, sequenced and their comparison showed that the 180 bp Bfal fragment is a part of the Msel sequence (Maniatis et al. 1982). Hence, only one co-segregating Mu-tagged site was detected.

Example 3

Analysis of the Mu-Tagged Site Present in the bx1::Mu Mutant

In addition to flanking primer sequences, the Msel fragment contained 267 bp with 90.6% percent homology to the maize trpA gene (Kramer et al., 1995). When the exon regions of the gene was compared, the DNA identity is 100%. The homologous region was located 3' to the Mu insertion site. The inventors then amplified the 5' flanking regions with Mu and trpA specific primers and carried out sequence analysis of the generated fragment (337 bp including Mu sequences), which revealed the 9 bp target site duplication characteristic for a Mu element insertion. As with the 3' flanking region, DNA homology was 100% when the exon regions of the trpA gene were compared. Hence, it can be concluded that indeed a Mu element was inserted in the Bx1 gene described herein in the bx1::Mu mutant. This conclusion was confirmed by the fact that a band shift, which co-segregated with the bx1::Mu allele was observed when trpA cDNA was the probe in Southern analysis. Trp A was mapped with the Recombinant Inbred system (Burr et al., 1991) and proved to be located on the short arm of chromosome 4 and within the limits of the method, was located at the same map position as CYP71C4 (Frey et al., 1995) By genetic analysis the Bx1 gene had been mapped to this region (Simcox et al., 1985).

Example 4

Structure of the bx1 Standard Mutant Gene

The full length cDNA of the Bx1 gene was isolated from a cDNA library of the maize line C131A (SEQ ID NO:1). This sequence was used to isolate the cDNA sequence of the standard bx1 mutant and the genomic sequences of this mutant and wildtype (C131A) allele (SEQ ID NO:4). The standard bx1 mutant carried a large deletion of 925 bp and comprised 360 bp of the 5' non-transcribed region, the first exon, the following intron and 52 bp of the second exon. 5'-race experiments demonstrated that the transcription started 26 bp downstream of the deletion end point. Sequence analysis of the full-size cDNA clone and the genomic sequence revealed that the exon joining in the mutant was the same as in the wild-type gene. The first ATG codon of the mature transcript was found in the wild-type gene reading frame and the deduced amino acid sequence displayed only one amino acid substitution beyond the deletion. However, since the first 162 amino acids of a total of 345 amino acids were missing, it was concluded that the truncated protein of the bx1 standard mutant had wild type function. This demonstrated that, as expected, mutations could be found in the Bx1 coding regions of the standard bx1 mutant, providing further evidence for the correct identification of the Bx1 gene herein.

Example 5

DIMBOA Is Synthesized in the bx1 Standard Mutant When Indole Is Applied

Indole was applied to pre-germinated etiolated seedlings of the bx1 standard mutant line and the endogenous compounds were analyzed by HPLC. As a control, seedlings were incubated in tryptophan in parallel. The analysis clearly revealed the presence of DIMBOA after application of indole, while feeding of tryptophan did not result in DIMBOA generation. This demonstrated that the mutation in the bx1 standard mutant was rescued by indole application. Therefore, the biosynthesis block was not downstream of indole formation. Further, the mutation was not upstream of indole formation since these compounds are essential for tryptophan synthesis, clearly implicating the Bx1 gene in the synthesis of indole.

Example 6

Transcript Differences of the Isolated Gene in Wild Type and bx1 Mutant Lines

Figure 4:
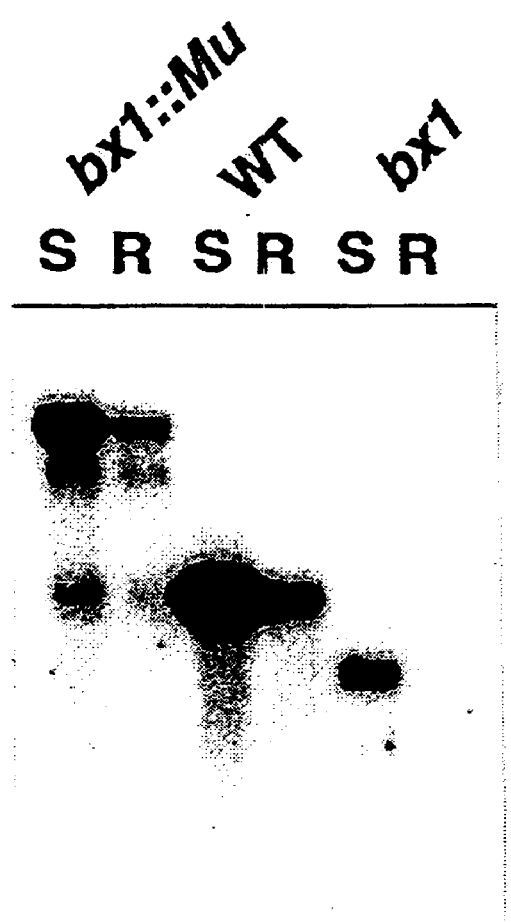
FIG. 4: Northern blot comparison of bx1 mutants to the Bx wild-type. S denotes shoot tissue, R is root tissue. The Mu bx1 insertional mutant, wild type Bx1, and standard bx1 mutant are indicated by bx1::Mu, WT and bx1, respectively. GADPH is a control for RNA loading.
Figure 4:
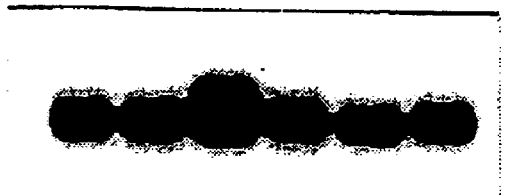
Figure 5:
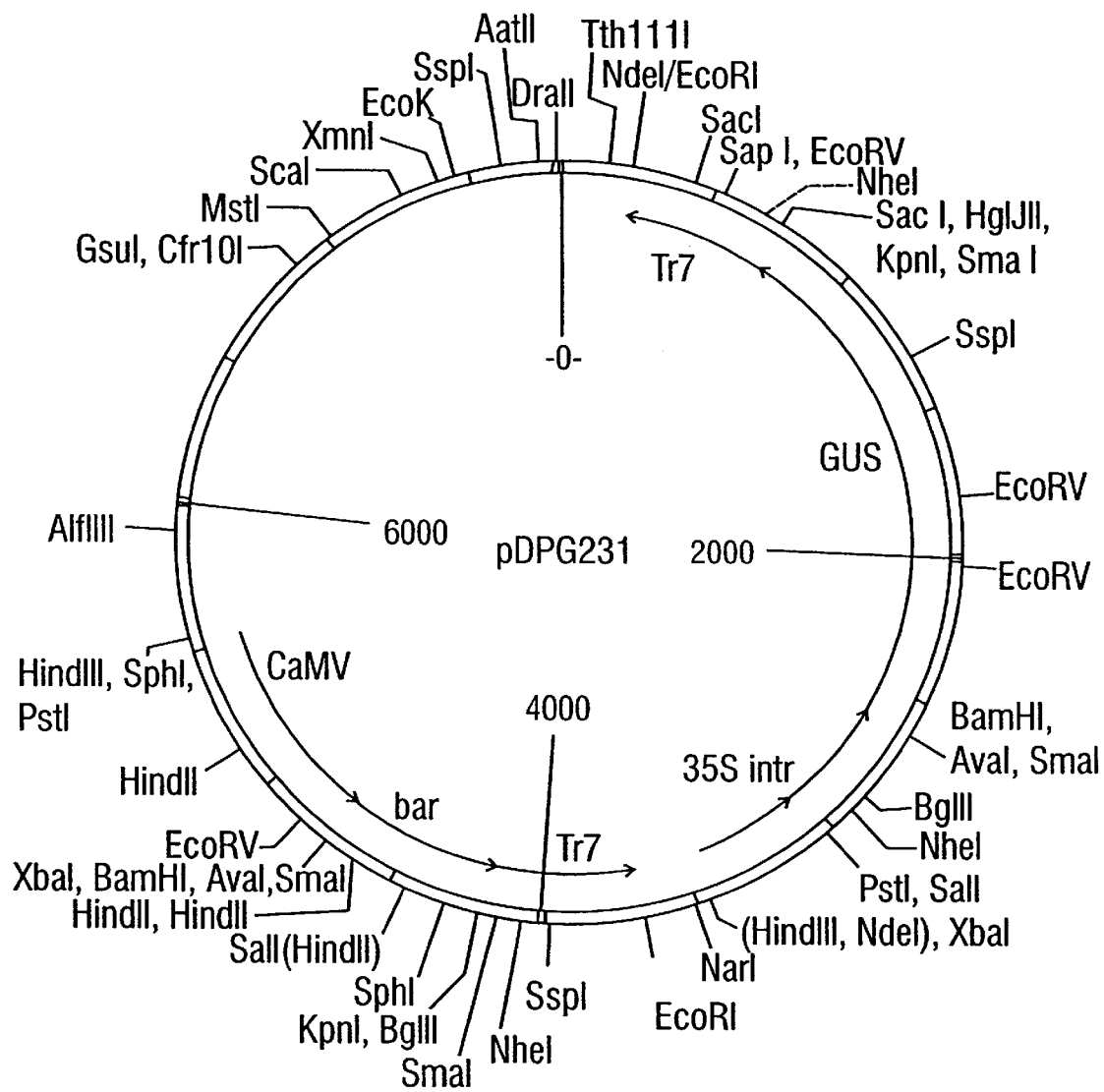
FIG. 5: Map of the bar gene carrying plasmid pDPG231. The expression cassette is isolated from the plasmid backbone by digesting the plasmid DNA with the restriction enzyme HindIII.
Figure 6:
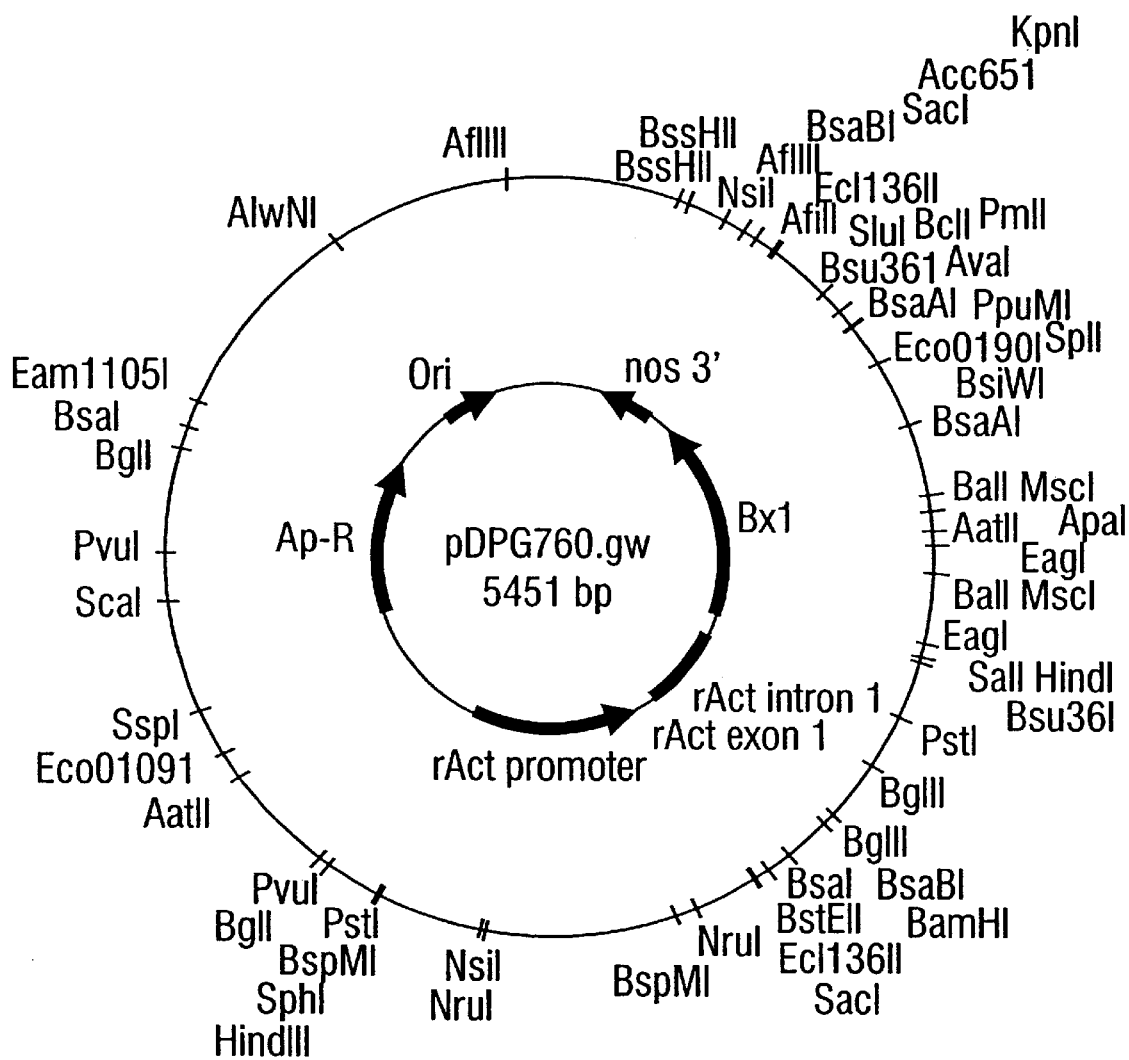
FIG. 6: Map of the Bx1 gene carrying plasmid pDPG760. The Bx1 gene is driven by the rice actin promoter linked to the rice actin intron. The terminator is from the nopaline synthase gene of *Agrobacterium tumefaciens*. The expression cassette is liberated from the plasmid backbone by digestion with the restriction enzymes HindIII and XbaI.

Northern analysis showed that the transcription of the gene started after imbibition of the kernel and high transcript levels were discovered in root and shoot of 5-days old etiolated seedlings. The mRNA levels of the wild type line C131A, the bx1::Mu and the bx1 standard mutant, were compared in 5-day old etiolated seedlings. A 1.6 kb transcript was detected in the wild type line, the transcript level in the shoot was higher as in the root (FIG. 4). In the Mu-insertion mutant the relation between shoot and root transcript level was comparable, however, the main transcript was about 2 kb larger and two minor transcripts were displayed. One of these was approximately the size of the wild type transcript. The transcript of the standard mutant line was about 0.6 kb smaller. The transcription pattern deviated in the bx1 standard mutant, in that almost no transcript was detectable in the root tissue. The transcription pattern of the closely linked CYP71C4 gene is not altered in the in this mutant. The results again, clearly indicated the correct identification of Bx1 herein.

Example 7

Complementation of the Standard bx1 Mutant With Indole

Figure 2C:
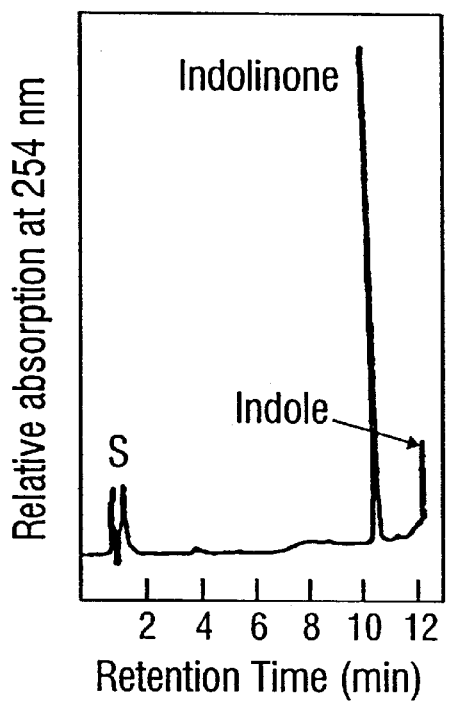
Figure 2D:
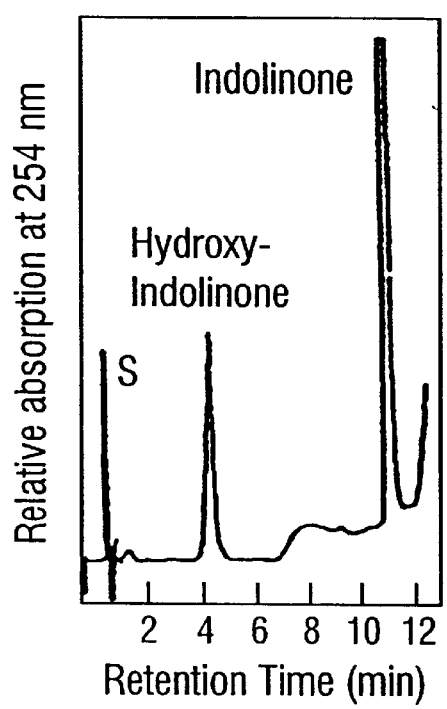
Figure 2E:
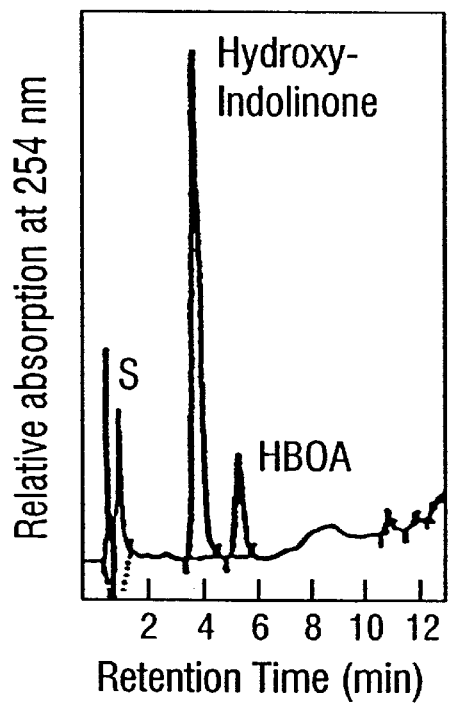
Figure 2F:
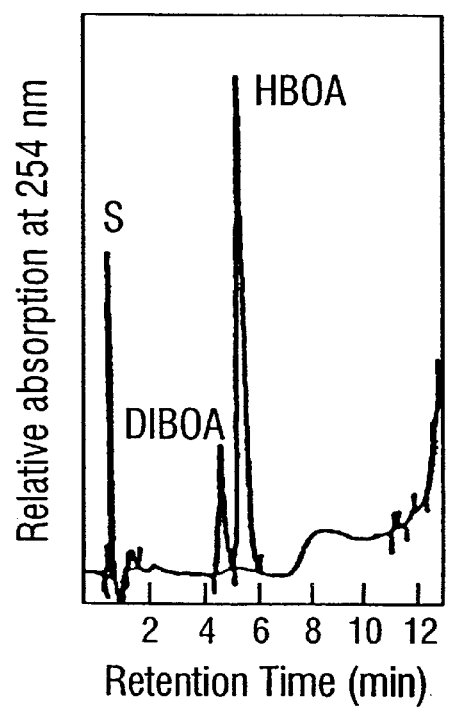

Further evidence for the identification of the Bx1 gene was provided by the complementation of the standard bx1 mutant with indole. It was predicted that the bx1 mutant should be defective in the production of free indole, and thus, that administration of indole should cause restoration of the wild-type phenotype. A study was therefore carried out to complement the standard bx1 mutant with indole. The immersion of shoots of bx1 seedlings (4 days after imbibition) into a 1 mM solution of indole in the dark for one day, clearly restored the formation of DIMBOA (FIG. 2A). Hence, the biosynthetic block in the bx1 mutant was not downstream of indole formation. Feeding of tryptophan, however, did not result in DIMBOA accumulation (FIG. 2B). When [3-$^{13}$C]indole (90% enrichment) was administered to maize shoots, [2-$^{13}$C]DIMBOA (66% enrichment) was recovered. This confirms that indole is an intermediate in the biosynthesis of DIMBOA.(Desai et al., 1996) and clearly implicates Bx1 in the production of indole.

Example 8

Elucidation of the Biosynthesis of DIMBOA From Indole: Bx2–Bx5

Genomic clones representing the published sequences of Bx2–Bx5 (Genbank Accession Numbers: Y11368, Y11404, X81828, Y11403) were isolated from a λ library, which was commercially available from Stratagene, using the CYP71 C1 clone as a probe. Bx2–Bx5 were then sequenced as described by Frey, et al., 1995. Comparison of the genomic DNA sequences to the cDNA sequences yielded the exon/intron structure of the genes. In order to study the function of the four P450 enzymes in the DIMBOA pathway, the yeast expression system established by Truan et al. (1993) was used. The cDNAs of Bx2–Bx5 were each inserted into the pYeDP60 expression vector (Urban et al., 1994). These constructs were individually used to transform the WAT11 yeast strain. In WAT11, a galactose inducible *Arabidopsis thaliana* microsomal NADPH-P450 reductase (ATR1) replaces the yeast reductase (Pompon et al., 1996).

Microsomes were isolated from the transgenic yeast strains and tested for enzymatic activity (Truan et al., 1993; Pompon et al., 1996). Results demonstrated that indole was converted to DIBOA by the stepwise action of four cytochrome P450 enzymes (FIG. 3). Incubation of yeast microsomes containing Bx2 protein with [3-13C]indole, resulted in the production of [3-13C]indolin-2-one as detected by HPLC. A sufficient amount of [3-13C]indolin-2-one was produced by this enzyme catalyzed reaction, in order to be used to study subsequent enzymatic conversions. When the [3-13C]indolin 2-one was used to treat microsomes containing the Bx3 protein, [3-13C]hydroxy-indolin-2-one was produced. For further analysis, unlabeled 3-hydroxy-indolin-2-one was obtained by reduction of commercially available isatin (indole-2,3-dione) in a yeast culture followed by HPLC (high pressure liquid chromatography) purification and confirmation of the structure of the 3-hydroxy-indolin-2-one by $^1$H NMR (nuclear magnetic resonance). Incubation of microsomes containing Bx4 with 3-hydroxy-indolin-2-one resulted in production of HBOA. Finally, HBOA was converted to DIBOA by microsomes containing Bx5. This reaction was previously described for maize microsomes (Bailey et al., 1991). The identity of the reaction products was confirmed by cochromatography with the authentic substances and by their UV spectra. The reaction products indolin-2-one and 3-hydroxy-indolin-2-one were further identified by their 1H-NMR-spectra. The identity of HBOA and DIBOA was corroborated by GC/MS analysis (Woodward et al., 1979). These results clearly demonstrated that the enzymatic activities of Bx2, Bx3, Bx4, and Bx5 catalyzed the production of DIBOA from indole.

Example 9

Cloning of a Duplicate Trp A Gene

A duplicate tryp alpha synthase gene was cloned (SEQ ID NO:3) by hybridization to the Bx1 cDNA (SEQ ID NO:1). This gene is presumably involved in tryptophan biosynthesis. TrpA Activity is required for the biosynthesis of the secondary plant metabolite DIMBOA in maize. The ability to isolate an additional allele encoding TrpA activity indicates that this locus has been duplicated during maize evolution and further suggests that multiple enzymes code for TrpA.

Example 10

Protocol for Amplifying Mu-Tagged Sequences

The protocol is based on the AFLP method developed by Keygene (Zabeau and Voss, European Patent application 92402629). In contrast to their protocol a linear Mu-specific amplification is made and the product isolated. Exponential amplification is performed with a Mu-specific nested primer and a primer complementary to a ligated adapter sequence. The complexity of the generated fragments is reduced by addition of one nucleotide (G/A/C/T) at the 3' end (first sequence specific nucleotide) of adapter and/or nested Mu primer.

1) Primer and adapter sequences ('-3' orientation)

```
MseI/BfaI Adapter:  TACTCAGGACTCAT
                    GACGATGAGTCCTGAG
Mu-Bio:             AGAGAAGCCAACGCCA(A/T)CGCCTCCATT
```

```
Msel Sel/A(GCT):    GATGAGTCCTGAGTAA/A(GCT)

Bfal Sel/A(GCT):    GATGAGTCCTGAGTAG/A(GCT)

Mu Sel:             TCTATAATGGCAATTATCTC
```

2) Restriction/ligation of genomic DNA

| 500 ng DNA | 1xRL 10 mM Tris-Acetate, pH 7.5 |
|---|---|
| 5 U MseI or BfaI | 10 mM Mg-Acetate |
| 40 µl volume | 50 mM K-Acetate |
| lxRL-Buffer | 50 ng/µl BSA | add
1 µl 50 µM MseI or BfaI adapter
1 µl 10×Ligation Buffer (Boehringer)
1 U T4-DNA Ligase
H$_2$O to a final volume of 50 µl
1 h RT, at least 2 h 37° C.
3) Mu-specific Amplification (linear, 12 cycles*)
27.5 µl DNA
2.5 µl 12 µM Mu-Biotin primer
10 µl 2.5 mM dNTPs (each)
5 µl 10×KCl V buffer
1 u Taq Polymerase (Boehringer)
Final volume of 50 µl, cover with paraffin

| PCR program: | |
|---|---|
| 1: 94° C. | 3 min |
| 2: 94° C. | 1 min |
| 3: 65° C. | 30 sec |
| 4: 72° C. | 60 sec |
| cycle 4 to 2 11x | |
| 6: 72° C. | 3 min |

Do not make more than 12 cycles, because this may yield aberrant exponential PCR amplification remove excess Mu-Biotin primer with QIA-quickspin column:
add 250 µl PB buffer to 50 µl PCR reaction, spin
wash column with 2×600 µl PE
elute with 50 µl TE, pH 8.5
add 50 µl 4 M NaCl to 50 µl eluat
(see Qiagen protocol for details)
4) Binding to Streptavidin Beads
  Suspend Streptavidin Dynabeads and transfer 10 µl to an Eppendorf tube remove storage buffer on Dynal MPC magnet wash with 100 µl Wash/Binding buffer add PCR solution, suspend beads, keep at RT for 30 min, resuspend occasionally.
Wash
2×with 100 µl Wash/Binding buffer,
2×with 100 µl T0.1E, store at 4° C.
(see Dynal protocol for details)
5) End-labeling of Mu Sel
  For 20 PCR reactions:
2.5 µl 10 µM Mu Sel
5 µl Gamma ATP (50 uCi)
1.25 µl One Phor All+buffer (Pharmacia)
1–2.5 units T4 Polynucletid Kinase total volume of 12.5 µl
30 min 37°, 10 min 70° C., spin down briefly, use directly for PCR
6) Exponential PCR With Labeled Primer
5 µl beads/DNA (suspend well before pipetting)
0.5 µl labeled Mu Sel Primer
0.6 µl MseI Sel/N or BfaI Sel/N, 10 µM
4.0 µl 2.5 mM dNTPs
2.0 µl 10×Ammonium sulphate buffer
2.0 µl BSA 1 mg/ml
final volume 17 µl, cover with paraffin

| PCR program: | | |
|---|---|---|
| 1) | 94° C. | pause |
| | | add 1 u Taq polymerase in 3 µl volume and continue |
| 2) | 94° C. | 1 min |
| 3) | 65° C. | 30 sec |
| | | decrease by 0.7° C. every cycle |
| 4) | 72° C. | 1 min |
| | | cycle 4 to 2 18x |
| 5) | 94° C. | 1 min |
| 6) | 52° C. | 30 sec |
| 7) | 72° C. | 1 min |
| | | cycle 7 to 5 26x |
| 8) | 72° C. | 3 min |

7) Analysis On Sequencing Gels
mix PCR 1:1 with sequencing loading dye (50% formamide)
incubate 3 min 80° C.
load about 1–2 µl per slot on a 6% standard 40 cm sequencing get
run Xylene Cyanol dye about 25 cm
treat as usual, overnight exposure
  Remarks:
  The reaction can be checked with non-radioactive PCR: do the reaction as described in 6) but in a 50 µl volume and with 5 µl of each primer, Analyze 10–20 µl on a high percentage agarose gel (best is Metaphore agarose). PCR products should be visible.
  In our hands PCR products are made with KCl V or Ammonium sulphate buffer or with both buffers.
10×KCl V:
  100 mM Tris, pH 8.3
  500 mM KCl
  20 Mm MgCl$_2$
  30% DMSO
10×Ammonium sulphate buffer
  670 mM Tris, pH 8.8
  167 mM (NH$_4$)$_2$SO$_4$
  100 mM Beta-Mercaptoethanol
  67 mM MgCl$_2$
8) Elution of a PCR Band
  A specific PCR band is isolated by cutting out the band from a sequencing gel and elution of the DNA from the polyacrylamide slice. For this purpose one suitable CPR reaction is loaded in several adjacent slots on a 6% sequencing gel. The desired band is visualized by autoradiography and cut from the gel.
  Use:
  1) A sequencing gel that is not polymerized to the glass plate
  2) Do not fix and dry the gel
  3) Cover the gel with saran wrap, add radioactive marker points for orientation; expose overnight
  4) Cut the x-ray film where the band is and cut the gel slice with the band using this "window".
  5) Elute the DNA with about 40 µl of 0.5 M Ammonium acetate, 10 mM Mg-acetate, 1 mM EDTA, pH 8.0, 01% SDS. Crash the slice, vortex and incubate at 37° C. overnight. Spin, recover the supernatant, add the same volume of elution buffer and vortex, spin, combine the supernatants, spin again and remove the supernatant carefully. Precipitate the DNA with 2.5 volumes of ethanol, leave on ice 30 min and spin for 20 min. Wash the pellet with 70% ethanol and dissolve in 10 μl TE (per slot used).
6) Do a PCR reaction with 1–5 μl of DNA solution as described in 6) but in a volume of 50 μl and with 5 μl of the non-labeled primers.
7) Sub-clone the PCR band
8) Confirm the cloned fragment by comparison with the original PCR fragment.
For this:
Amplify the band from 1 ng of the plasmid by a PCR reaction using primers and conditions described in 6) but dilute the labeled primer (4 μl 1×One-Phore-All buffer, 0.2 μl of kinase reaction, 0.8 μl 10 uM Mu Sel, use 0.5 μl per reaction). Run sequencing gel with plasmid and plant DNA reaction.

Remark: Investigate several sub-clones, they might be checked for uniformity by restriction analysis prior to PCT amplification.

Example 11

Transformation of Maize With a Bx1 Gene Containing Construct

Maize plants of the genotype A188×B73 are crossed to Hi-II maize plants (Armstrong et al., 1991). Immature embryos (1.2–2.0 mm in length) are then excised from surface-sterilized, greenhouse-grown ears of Hi-II 11–12 days post-pollination. The Hi-II genotype was developed from an A188×B73 cross for high frequency development of type II callus from immature embryos (Armstrong et al., 1991). Approximately 30 embryos per petri dish are plated axis side down on a modified N6 medium containing 1 mg/l 2,4-D, 100 mg/l casein hydrolysate, 6 mM L-proline, 0.5 g/l 2-(N-morpholino)ethanesulfonic acid (MES), 0.75 g/l $MgCl_2$, and 2% sucrose solidified with 2 g/l Gelgro, pH 5.8 (#735 medium). Embryos are then cultured in the dark for two to four days at 24° C.

Approximately four hours prior to bombardment, embryos are transferred to the above culture medium with the sucrose concentration increased from 3% to 12%. When embryos are transferred to the high osmoticum medium they are arranged in concentric circles on the plate, starting 2 cm from the center of the dish, positioned such that their coleorhizal end is orientated toward the center of the dish. Usually two concentric circles are formed with 25–35 embryos per plate.

DNA may be precipitated onto gold particles as follows. A stock solution of gold particles is prepared by adding 60 mg of 0.7 μm gold particles to 1000 μl absolute ethanol and incubating for at least 3 hours at room temperature followed by storage at −20 C. Twenty to thirty five μl sterile gold particles are centrifuged in a microcentrifuge for 1 min. The supernatant is removed and one ml sterile water is added to the tube, followed by centrifugation at 2000 rpm for 5 minutes. Microprojectile particles are resuspended in 30 μl of DNA solution (30 μg total DNA) containing 10 μg each of the desired vectors. Two hundred twenty microliters sterile water, 250 μl 2.5 M $CaCl_2$ and 50 μl spermidine are added. The mixture is thoroughly mixed and placed on ice for 4 minutes, then vortexed at 4 C. for 10 minutes, centrifuged at 500 rpm for 5 minutes and again placed on ice for 4 minutes. The supernatant is removed and the pellet resuspended in 600 μl absolute ethanol. Following centrifugation at 500 rpm for 5 minutes the pellet is resuspended in 36 μl of absolute ethanol. The particles are then allowed to settle for 0–4 minutes depending on particle size. For example, 0.6 μm gold particles are allowed to settle for 2 min whereas 0.7 μm gold particles are allowed to settle for 4 minutes. Ten μl of the particle preparation is then dispensed on the surface of a flyer disk and the ethanol is allowed to dry completely.

The plates containing embryos are placed on the third shelf from the bottom, 5 cm below the stopping screen in the bombardment chamber. Using the 1100 psi rupture disc, each plate of embryos is then bombarded once with the DuPont Biolistics PDS1000He particle bombardment device. Embryos are allowed to recover overnight on high osmotic strength medium prior to initiation of selection.

Following recovery on high osmoticum medium (735, 12% sucrose) overnight (16–24 hours), the embryos are then transferred to selection medium containing 1 mg/l bialaphos (#739, 735 plus 1 mg/l bialaphos or #750, 735 plus 0.2M mannitol and 1 mg/l bialaphos) and maintained in the dark at 24 C. After three to four week on the initial selection plates about 90% of the embryos will typically form Type II callus and will be transferred to selective medium containing 3 mg/l bialaphos (#758). Bialaphos resistant tissue is subcultured about every two weeks onto fresh selection medium (#758). Transformants can be confirmed using PCR analysis to detect presence of the Bx1 containing plasmid.

Transformants are regenerated as generally described in PCT publication WO 95/06128. Transformed embryogenic callus is transferred to regeneration culture medium (MS culture medium (Murashige and Skoog, 1962), containing 0.91 mg/L L-asparagine, 1.4 g/L L-proline, 20 g/L D-sorbitol, 0.04 mg/L naphthalene acetic acid (NAA) and 3 mg/L 6-benzylaminopurine). Cells are grown for about four weeks on this culture medium with a transfer to fresh medium at about 2 weeks. Transformants are subsequently transferred to MS0 culture medium (MS medium with no phytohormones added). Regenerated plants are then transferred to soil as described in U.S. patent application Ser. No. 08/763,704, filed Dec. 9, 1996.

Example 12

Confirmation of the Role of the Bx1 Protein in the Production of Free Indole From Indole-3-Glycerol Phosphate In bacteria, production of indole from indole-3-glycerol phosphate is almost completely dependent on formation of an active $\alpha_2\beta_2$ complex between tryptophan synthase α (TSA) and tryptophan synthase β (TSB), and indole is usually not released during tryptophan synthesis (Hyde et al., 1998). An analogous heterosubunit complex exists in Arabidopsis (Radwanski et al., 1995). If the Bx1 gene product catalyzes the formation of free indole from indole 3-glycerol phosphate, Bx1 should function independently of TSB. To demonstrate this assumption, the Bx1 polypeptide was expressed in *E. coli*, and then purified and assayed for steady-state kinetic constants (Creighton, 1970). The Bx1 protein was expressed in *E. coli* by inserting the Bx1 cDNA (SEQ ID NO:1) into a modified pET3a vector (Rosenberg et al., 1987). Transformed bacterial cells were grown and Bx1 was purified from the cells to homogeneity by means of a six-nucleotide oligomer COOH-terminal histidine tag (Qiagen, Inc., Ni-NTA purification system).

Isolation of indole-3-glycerol phosphate and fluorimetric enzymatic assays were done as follows. A reaction volume of 1 ml containing 4 μg of Bx1 protein, 50 μg of glyceraldehyde phosphate dehydrogenase, and 0.5 mM nicotinamide adenine dinucleotide (oxidized form) was incubated at 22° C. for 2 min. Indole-3-glycerol phosphate concentration varied from 0 to 50 μM. The identity of the product indole was proven by Ehrlich's reagent (Rosenberg et al. 1987). The Michaelis constant ($K_m^{indole\text{-}3\text{-}glycerol\ phosphate}$) was determined to be 0.013 mM and the catalytic rate constant ($k_{cat}$) to be 2.8 s$^{-1}$. Comparison of these values with the constants for conversion of indole-3-glycerol phosphate to indole by the native $E.\ coli\ \alpha_2\beta_2$ complex ($K_m^{indole\text{-}3\text{-}glycerol\ phosphate}$=0.027 mM, $k_{cat}$=0.2 s$^{-1}$) (Weischet et al., 1976) demonstrated that Bx1, independent of TSB, is ~30 times as efficient as the bacterial complex in catalyzing the production of indole. Further, the study confirmed the role of the Bx1 protein in the conversion of indole-3-glycerol phosphate to free indole (FIG. 3).

All of the composition and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

References

The following references, to the extent that they provide exemplary procedural or other details supplementary to those set forth herein, are specifically incorporated herein by reference.

U.S. Pat. No. 4,554,101, issued Nov. 19, 1985.
U.S. Pat. No. 4,683,195, issued Jul. 28, 1987.
U.S. Pat. No. 4,683,202, issued Jul. 28, 1987.
U.S. Pat. No. 4,757,011, issued Jul. 12, 1988.
U.S. Pat. No. 4,769,061, issued Sep. 6, 1988.
U.S. Pat. No. 4,940,835, issued Feb. 23, 1990.
U.S. Pat. No. 4,971,908, issued Nov. 20, 1990.
U.S. Pat. No. 5,384,253, issued Jan. 24, 1995.
U.S. Pat. No. 5,489,520
U.S. Pat. No. 5,538,880
U.S. Pat. No. 5,550,318, issued Aug. 27, 1996
U.S. Pat. No. 5,591,616,
U.S. patent application Ser. No. 08/113,561, filed Aug. 25, 1993
U.S. patent application Ser. No. 08/763,704, filed Dec. 9, 1996
European Pat. No. 0189707, published Aug. 6, 1986.
Abdullah et al., *Biotechnology*, 4:1087, 1986.
Bailey and Larson, *Plant Physiol.*, 95:792–796, 1991.
Benbrook et al., In: *Proceedings Bio Expo 1986*, Butterworth, Stoneham, Mass., pp. 27–54, 1986.
Burr and Burr, *Trends Genet.*, 7, 55, 1991.
Bytebier et al., *Proc. Natl. Acad. Sci. USA*, 84:5345, 1987.
Callis et al., *Genes and Development*, 1:1183, 1987.
Campos et al., *Chem. Ecol.*, 15:1989.
Capecchi, "High efficiency transformation by direct microinjection of DNA into cultured mammalian cells," *Cell* 22(2):479–488, 1980.
Cashmore et al., *Gen. Eng. of Plants*, Plenum Press, New York, 29–38, 1983.
Chau et al., *Science*, 244:174–181, 1989.
Chomet, In *the Maize Handbook*, Freeling and Walbot, Eds. (Springer-(Verlag, New York, 1994), 243–248.
Clapp, "Somatic gene therapy into hematopoietic cells. Current status and future implications," *Clin. Perinatol.* 20(1):155–168, 1993.
Couture et al., *Physiol. Plant Pathol.*, 1:515–521, 1971.
Cristou et al., *Plant Physiol*, 87:671–674, 1988.
Cuevas et al., *Phytochemistry*, 29,1429–1432, 1990.
Curiel et al., "Adenovirus enhancement of transferrin-polylysine-mediated gene delivery," *Proc. Natl. Acad. Sci. USA* 88(19):8850–8854, 1991.
Curiel et al., "High-efficiency gene transfer mediated by adenovirus coupled to DNA-polylysine complexes," *Hum. Gen. Ther.* 3(2):147–154, 1992.
Desai, *Chem. Commun.*, 1321, 1996.
Dhir et al., *Plant Cell Reports*, 10:97, 1991
Dunn et al., *Can. J. Plant Sci.*, 61:583, 1981.
Eglitis et al., "Retroviral-mediated gene transfer into hemopoietic cells," *Avd. Exp. Med. Biol.* 241:19–27, 1988.
Fraley et al., *Biotechnology*, 3:629, 1985.
Fraley et al., *Proc. Natl. Acad. Sci. USA*, 80:4803, 1983.
Frey et al., *Mol. Gen. Genet.*, 246,100, 1995.
Fromm et al., "Expression of genes transferred into monocot and dicot plant cells by electroporation," *Proc. Natl. Acad. Sci. USA* 82(17):5824–5828, 1985.
Fromm et al., *Nature* 312:791–793, 1986.
Fujimura et al., *Plant Tissue Culture Letters*, 2:74, 1985.
Fynan et al., "DNA vaccines: protective immunizations by parenteral, mucosal, and gene gun inoculations," *Proc. Natl. Acad. Sci. USA* 90(24):11478–11482, 1993.
Graham and van der Eb, "Transformation of rat cells by DNA of human adenovirus 5," *Virology* 54(2):536–539, 1973.
Hamilton, *Weeds*, 12:27–30, 1964.
Helentjaris et al., *Genetics*, 118,353, 1989.
Hess, *Intern Rev. Cytol.*, 107:367, 1987.
Horsch et al., *Science*, 227:1224–1231, 1985.
Johnston and Tang, "Gene gun transfection of animal cells and genetic immunization," *Methods Cell. Biol.* 43(A): 353–365, 1994.
Jorgensen et al., *Mol. Gen. Genet.*, 207:471, 1987.
Klee et al., *Biotechnology*, 3:637–642, 1985.
Keller et al., *EMBO J.*, 8:1309–14, 1989.
Klein et al., *Nature*, 327:70, 1987.
Klein et al., *Proc. Natl. Acad. Sci. USA*, 85:8502–8505, 1988.
Klun et al., *Econ. Entomol.*, 60:1529–1533, 1967.
Konieczny and Ausubel, *Plant J.*, 4, 403, 1993.
Kramer and Koziel, *Plant Mol. Biol.*, 27, 1183, 1995.
Kutchan, *Plant Cell*, 7:1059, 1995.
Kyte and Doolittle, A simple method for displaying the hydropathic character of a protein," *J. Mol. Biol.* 157(1): 105–132, 1982.
Langridge et al., *Proc. Natl. Acad. Sci. USA*, 86:3219–3223, 1989.
Lindstrom et al., *Developmental Genetics*, 11:160, 1990.
Long et al., *Crop Sci.*, 14: 601, 1974
Long et al., *Crop Sci.*, 17:55–58, 1977.
Lorz et al., *Mol. Gen. Genet.*, 199:178, 1985.
Lu et al., "High efficiency retroviral mediated gene transduction into single isolated immature and replatable CD34(3+) hematopoietic stem/progenitor cells from human umbilical cord blood," *J. Exp. Med.* 178(6):2089–2096, 1993.
Luo et al., *Plant Mol. Biol. Reporter*, 6:165, 1988.

Maddock et al., *Third International Congress of Plant Molecular Biology*, Abstract 372, 1991.
Maniatis et al. *Molecular Cloning*, Cold Spring Harbor Laboratory, Sec. Ed. (1989)
Marcotte et al., *Nature*, 335:454, 1988.
McCabe et al., *Biotechnology*, 6:923, 1988.
Neuhaus et al., *Theor. Appl. Genet.*, 75:30, 1987.
Niemeyer et al., *Photochemistry*, 27:3349–3358, 1988.
Odell et al., *Nature*, 313:810, 1985.
Omirulleh et al., *Plant Molecular Biology*, 21:415–428, 1993.
Pena et al., *Nature*, 325:274, 1987.
Pompon et al., *Methods Enzymology*, 272,51, 1996.
Poszkowski et al., *EMBO J.*, 3:2719, 1989.
Potrykus et al., *Mol. Gen. Genet.*, 199:183, 1985.
Poulsen et al., *Mol. Gen. Genet.*, 205:193–200, 1986.
Radwanski et al., *Mol. Gen. Genet.*, 248, 657, 1995.
Rogers et al., In: *Methods For Plant Molecular Biology*, A. Weissbach and H. Weissbach, eds., Academic Press Inc., San Diego, Calif. 1988.
Rogers et al., *Meth. in Enzymol.*, 153:253–277, 1987.
Simcox and Weber, *Crop. Sci.*, 25:827–830, 1985.
Simpson, *Science*, 233:34, 1986.
Smith et al., *EMBO J.*, 9,741, 1990.
Spielmann et al., *Mol. Gen. Genet.*, 205:34, 1986.
Sprague G. and Dudley J. W. (eds.), "Corn and Improvement", Third Ed., *American Society of Agronomy*, 1988.
Sullivan et al., *Env. Ent.*, 3:718–720,1974.
Toriyama et al., *Theor Appl. Genet.*, 73:16, 1986.
Truan et al., *Gene*, 125,49, 1993.
Uchimiya et al., *Mol. Gen. Genet.*, 204:204, 1986.
Urban et al., *Eur. J. Biochem.*, 222,843, 1994.
Van Tunen et al., *EMBO J.*, 7:1257, 1988.
Vasil et al., "Herbicide-resistant fertile transgenic wheat plants obtained by microprojectile bombardment of regenerable embryogenic callus," *Biotechnology*, 10:667–674, 1992.
Vasil, *Biotechnology*, 6:397, 1988.
Vodkin et al., *Cell*, 34:1023, 1983.
Vogel et al., *J. Cell Biochem.*, supplement 13D:312, 1989.
Wagner et al., "Coupling of adenovirus to transferrin-polylysine/DNA complexes greatly enhances receptor-mediated gene delivery and expression of transfected genes," *Proc. Natl. Acad. Sci. USA* 89 (13):6099–6103, 1992.
Walross and Virtanen, *Acta Chem. Scand.*, 13:1906–1908, 1959.
Watson S. and Ramstad P. E. (eds), "Corn: Chemistry and Technology", *American Association of Cereal Chemists*, 1987.
Weissbach and Weissbach, *Methods for Plant Molecular Biology*, (eds.), Academic Press, Inc., San Diego, Calif., 1988.
Wenzler et al., *Plant Mol. Biol.*, 12:41–50, 1989.
Wong and Neumann, "Electric field mediated gene transfer," *Biochim. Biophys. Res. Commun.* 107(2):584–587, 1982.
Woodward et al., *Plant Physiol.*, 63,9, 1979.
Wright et al., *Plant Cell*, 4,711, 1992.
Yamada et al., *Plant Cell Rep.*, 4:85, 1986.
Yang et al., *Proc. Natl. Acad. Sci. USA*, 87:4144–48, 1990.
Yu et al., *Appl. Environ. Microbiol.*, 61,2365, 1995.
Zatloukal et al., "Transferrinfection: a highly efficient way to express gene constructs in eukaryotic cells," *Ann. N.Y. Acad. Sci.*, 660:136–153, 1992.
Zhou et al., *Methods in Enzymology*, 101:433, 1983.

---

What is claimed is:

1. An isolated nucleic acid encoding a maize Bx1 polypeptide having the amino acid sequence of SEQ ID NO:2 linked operably to a promoter functional in plants, wherein said promoter is not the native Bx1 promoter.

2. The isolated nucleic acid claim 1, wherein said Bx1 polypeptide comprises a transit peptide having the amino acid sequence set forth as residue 1 to about bases 85–100 of SEQ ID NO:1.

3. The isolated nucleic acid of claim 1, wherein said nucleic acid comprises the nucleotide sequence set forth in SEQ ID NO:1.

4. The isolated nucleic acid of claim 1, further comprising a selectable marker gene.

5. The isolated nucleic acid of claim 1, further comprising plasmid DNA.

6. The isolated nucleic acid of claim 1, wherein said promoter is functional in a monocot.

7. The isolated nucleic acid of claim 6, wherein said monocot is selected from the group consisting of wheat, maize, rye, rice, turfgrass, sorghum, millet and sugarcane.

8. The isolated nucleic acid of claim 7, wherein said promoter is functional in maize.

9. The isolated nucleic acid sequence of claim 1, wherein said promoter is not functional in seed.

10. The isolated nucleic acid of claim 1, wherein said promoter is selected from the group consisting of CaMV 35S, CaMV 19S, nos, Adh, actin, histone, ribulose bisphosphate carboxylase, R-allele, root cell promoter, α-tubulin, ABA-inducible promoter, turgor-inducible promoter, rbcS, corn sucrose synthetase 1, corn alcohol dehydrogenase 1, corn light harvesting complex, corn heat shock protein, pea small subunit RuBP carboxylase, Ti plasmid mannopine synthase, Ti plasmid nopaline synthase, petunia chalcone isomerase, bean glycine rich protein 1, CaMV 35s transcript, Potato patatin, actin, cab, PEPCase and S-E9 small subunit RuBP carboxylase promoter.

11. The isolated nucleic acid of claim 9, wherein said promoter is selected from the group consisting of ribuolose bisphosphate carboxylase, root cell promoter, α-tubulin, corn light harvesting complex, pea small subunit RuBP carboxylase, cab, PEPCase and S-E9 small subunit RuBP carboxylase promoter.

12. A transgenic plant cell stably transformed with at least a first transgene comprising a nucleic acid sequence encoding a maize Bx1 polypeptide having the amino acid sequence of SEQ ID NO:2 linked operably to a promoter functional in plants, wherein said promoter is not the native Bx1 promoter.

13. The transgenic plant cell of claim 12, wherein said promoter is not functional in the seeds of plants.

14. The transgenic plant cell of claim 12, wherein said promoter is selected from the group consisting of CaMV 35S, CaMV 19S, nos, Adh, actin, histone, ribulose bisphosphate carboxylase, R-allele, root cell promoter, α-tubulin, ABA-inducible promoter, turgor-inducible promoter, rbcS, corn sucrose synthetase 1, corn alcohol dehydrogenase 1, corn light harvesting complex, corn heat shock protein, pea small subunit RuBP carboxylase, Ti plasmid mannopine synthase, Ti plasmid nopaline synthase, petunia chalcone isomerase, bean glycine rich protein 1, CaMV 35s transcript, Potato patatin, actin, cab, PEPCase and S-E9 small subunit RuBP carboxylase promoter.

15. The transgenic plant cell of claim 13, wherein said plant cell is derived from a monocot.

16. The transgenic plant cell of claim 15, wherein said monocot is selected from the group consisting of wheat, maize, rye, cotton, turfgrass, rice, sorghum, millet and sugarcane.

17. The transgenic plant cell of claim 13, wherein said plant cell is derived from a dicot.

18. The transgenic plant cell of claim 17, wherein said dicot is selected from the group consisting of tobacco, cotton, soybean, canola, tomato and potato.

19. The transgenic plant cell of claim 13, further comprising a nucleic acid sequence encoding a polypeptide selected from the group consisting of Bx2, Bx3, Bx4 and Bx5.

20. The transgenic plant cell of claim 13, further comprising at least a first selectable marker gene.

21. A fertile transgenic plant stably transformed with at least a first transgene comprising a nucleic acid sequence encoding a maize Bx1 polypeptide having the amino acid sequence of SEQ ID NO:2 linked operably to a promoter functional in plants, wherein said promoter is not the native Bx1 promoter.

22. The fertile transgenic plant of claim 21, wherein said promoter is not functional in the seeds of plants.

23. The fertile transgenic plant of claim 21, wherein said promoter is selected from the group consisting of CaMV 35S, CaMV 19S, nos, Adh, actin, histone, ribulose bisphosphate carboxylase, R-allele, root cell promoter, α-tubulin, ABA-inducible promoter, turgor-inducible promoter, rbcS, corn sucrose synthetase 1, corn alcohol dehydrogenase 1, corn light harvesting complex, corn heat shock protein, pea small subunit RuBP carboxylase, Ti plasmid mannopine synthase, Ti plasmid nopaline synthase, petunia chalcone isomerase, bean glycine rich protein 1, CaMV 35s transcript, Potato patatin, actin, cab, PEPCase and S-E9 small subunit RuBP carboxylase promoter.

24. The fertile transgenic plant of claim 21, wherein said plant is a monocot.

25. The fertile transgenic plant of claim 24, wherein said monocot is selected from the group consisting of wheat, maize, rye, cotton, rice, sorghum, millet and sugarcane.

26. The fertile transgenic plant of claim 25, wherein the monocot is maize.

27. The fertile transgenic plant of claim 21, wherein said plant is a dicot.

28. The fertile transgenic plant of claim 27, wherein the dicot is selected from the group consisting of tobacco, cotton, soybean, canola, tomato and potato.

29. The fertile transgenic plant of claim 21, further comprising a nucleic acid sequence encoding a polypeptide selected from the group consisting of Bx2, Bx3, Bx4 and Bx5.

30. The fertile transgenic plant of claim 21, further comprising at least a first selectable marker gene.

31. The fertile transgenic plant of claim 21, wherein said transgene is transmitted through a complete normal sexual cycle of the transgenic plant to the next generation.

32. A seed from the plant of claim 31, wherein said seed has inherited said transgene.

33. A fertile transgenic plant produced by growing the seed of claim 32.

34. A progeny plant of any generation of the transgenic plant of claim 33, wherein said progeny plant has inherited said transgene.

35. The fertile transgenic plant of claim 21, further defined as a *Zea mays* plant exhibiting resistance to insect infestation, herbicide damage or disease as a result of having a genome stably transformed with said transgene.

36. The *Zea mays* plant of claim 35, wherein said insect infestation is caused by a pest selected from the group consisting of *Helminthosporium turcicum, Rhophalosiphum maydis, Diplodia maydis* and *Ostrinia nubilalis*.

37. The *Zea mays* plant of claim 35, wherein said transgene is transmitted through a complete normal sexual cycle of the transgenic plant to the next generation.

38. A seed of the plant of claim 37, wherein said seed has inherited said transgene.

39. A transgenic plant produced by growing the seed of claim 38.

40. A progeny *Zea mays* plant of any generation of the transgenic plant of claim 39, wherein said progeny plant has inherited said transgene.

41. The progeny *Zea mays* plant of claim 40, further comprising a transgenic nucleic acid sequence encoding a polypeptide selected from the group consisting of Bx2, Bx3, Bx4, and Bx5.

42. A method for producing a plant resistant to pest infestation comprising:
  (i) stably transforming a starting plant cell with a nucleic acid sequence encoding a maize Bx1 polypeptide having the amino acid sequence of SEQ ID NO:2, wherein said nucleic acid sequence is linked operably to a promoter functional in a plant cell; and
  (ii) regenerating the stably transformed cell into a fertile transgenic plant in which the introduced Bx1 gene expresses the maize Bx1 polypeptide, thereby increasing the benzoxazinone content of transformed cells of said plant,
whereby the resistance of said fertile transgenic plant to pest infestation is increased relative to a plant regenerated from the starting plant cell.

43. The method of claim 42, wherein said benzoxazinone is 2,4-dihydroxy-7-methoxy-1,4-benzoxazin-3-one.

44. The method of claim 42, wherein said pest infestation is caused by a pest selected from the group consisting of *Helminthosporium turcicum, Rhophalosiphum maydis, Diplodia maydis* and *Ostrinia nubilalis*.

45. The method of claim 42, wherein said starting plant cell is from a monocot.

46. The method of claim 45, wherein said monocot is selected from the group consisting of wheat, maize, rye, rice, turfgrass, sorghum, millet and sugarcane.

47. The method of claim 42, wherein said starting plant cell is from a dicot.

48. The method of claim 47, wherein said dicot is selected from the group consisting of tobacco, tomato, potato, soybean and cotton.

49. The method of claim 42, further comprising transforming said stably transformed starting plant cell with a DNA encoding a polypeptide selected from the group consisting of Bx2, Bx3, Bx4 and Bx5.

50. The method of claim 42, wherein said starting plant cell is transformed by a method selected from the group consisting of electroporation, microinjection, microprojectile bombardment and liposomal encapsulation.

51. The method of claim 50, further comprising stably transforming said starting plant cell with at least a first selectable marker gene.

52. The method of claim 51, wherein said first selectable marker gene encodes a protein is selected from the group consisting of phosphinothricin acetyltransferase, glyphosphate resistant EPSPS, aminoglycoside phosphotransferase, hygromycin phosphotransferase, dalapon dehalogenase, bromoxynil resistant nitrilase and anthranilate synthase.

53. A method of producing a transgenic seed capable of growing a plant with enhanced benzoxazinone biosynthesis comprising:
  (i) obtaining a first and a second seed, wherein one or both of said first and second seeds comprises a transgene comprising a nucleic acid sequence encoding a maize Bx1 polypeptide having the amino acid sequence of SEQ ID NO:2, wherein said first and second seeds are from sexually compatible plant species;
  (ii) planting said first and second seeds and allowing said first and second seeds to grow into sexually mature first and second parent plants;
  (iii) allowing cross-pollination to occur between said first and second plants; and
  (iv) collecting at least a first transgenic seed resulting from said cross-pollination, wherein said seed has inherited said transgene from said first or second parent plant.

54. The method of claim 53, wherein said sexually compatible species is a monocot plant species.

55. The method of claim 54, wherein said monocot plant species is selected from the group consisting of wheat, maize, rye, rice, turfgrass, sorghum, millet and sugarcane.

56. The method of claim 55, wherein said sexually compatible plant species is a dicot plant species.

57. The method of claim 56, wherein said dicot plant species is selected from the group consisting of tobacco, tomato, potato, soybean and cotton.

58. The method of claim 53, wherein said first or second seeds further comprise a transgene encoding a polypeptide selected from the group consisting of Bx2, Bx3, Bx4 and Bx5.

59. The transgenic plant cell of claim 13, wherein said promoter is selected from the group consisting of ribuolose bisphosphate carboxylase, root cell promoter, α-tubulin, corn light harvesting complex, pea small subunit RuBP carboxylase, cab, PEPCase, and S-E9 small subunit RuBP carboxylase promoter.

60. The fertile transgenic plant of claim 22, wherein said promoter is selected from the group consisting of ribuolose bisphosphate carboxylase, root cell promoter, α-tubulin, corn light harvesting complex, pea small subunit RuBP carboxylase, cab, PEPCase, and S-E9 small subunit RuBP carboxylase promoter.

* * * * *

UNITED STATES PATENT AND TRADEMARK OFFICE
CERTIFICATE OF CORRECTION

PATENT NO.   : 6,331,660 B1  
DATED        : December 18, 2001  
INVENTOR(S)  : Chomet et al.

Page 1 of 1

It is certified that error appears in the above-identified patent and that said Letters Patent is hereby corrected as shown below:

<u>Column 74,</u>
Line 15, please delete "protein is" and insert -- protein -- therefor.

Signed and Sealed this

Twenty-third Day of April, 2002

Attest:

Attesting Officer

JAMES E. ROGAN
*Director of the United States Patent and Trademark Office*

SEQUENCE LISTING

```
<160> NUMBER OF SEQ ID NOS:  4

<210> SEQ ID NO 1
<211> LENGTH: 1508
<212> TYPE: DNA
<213> ORGANISM: Artificial Sequence
<220> FEATURE:
<221> NAME/KEY: CDS
<222> LOCATION: (49)..(1089)
<223> OTHER INFORMATION: Description of Artificial Sequence:  Synthetic
      Primer

<400> SEQUENCE: 1
gaattcccga aggaggaacg aacggacagg ttgttgcaca gaagcgac atg gct ttc        57
                                                    Met Ala Phe
                                                      1 gcg ccc aaa acg tcc tcc tcc tcc tcg ctc tcc tcg gcg ttg cag gca      105
Ala Pro Lys Thr Ser Ser Ser Ser Ser Leu Ser Ser Ala Leu Gln Ala
      5                  10                  15 gct cag tcg ccg ccg ctg ctc ctg agg cgg atg tcg tcg acc gca aca      153
Ala Gln Ser Pro Pro Leu Leu Leu Arg Arg Met Ser Ser Thr Ala Thr
 20                  25                  30                  35 ccg aga cgg agg tac gac gcg gcc gtc gtc gtc act acc acc act          201
Pro Arg Arg Arg Tyr Asp Ala Ala Val Val Val Thr Thr Thr Thr
                 40                  45                  50 gct aga gct gct gcg gct gct gtc acg gtt ccc gcc gcc ccg ccg cag      249
Ala Arg Ala Ala Ala Ala Ala Val Thr Val Pro Ala Ala Pro Pro Gln
                 55                  60                  65
```

```
gcg ccg gcg ccg gcg ccg gtg ccg cca aag caa gcg gcg gca ccc gcc        297
Ala Pro Ala Pro Ala Pro Val Pro Pro Lys Gln Ala Ala Ala Pro Ala
         70                  75                  80 gag agg agg agc cgt ccg gtg tcg gac acc atg gcg gcg ctc atg gcc        345
Glu Arg Arg Ser Arg Pro Val Ser Asp Thr Met Ala Ala Leu Met Ala
     85                  90                  95 aag ggc aag acc gcg ttc atc ccg tac atc acc gcc ggc gac ccc gac        393
Lys Gly Lys Thr Ala Phe Ile Pro Tyr Ile Thr Ala Gly Asp Pro Asp
100                 105                 110                 115 cta gcg acg acg gcc gag gcg ctg cgg ctg ctg gac ggc tgt ggc gcc        441
Leu Ala Thr Thr Ala Glu Ala Leu Arg Leu Leu Asp Gly Cys Gly Ala
                120                 125                 130 gac gtc atc gag ctg ggc gtg ccc tgc tcg gac ccc tac atc gac ggg        489
Asp Val Ile Glu Leu Gly Val Pro Cys Ser Asp Pro Tyr Ile Asp Gly
            135                 140                 145 ccc atc atc cag gcg tcg gtg gcg cgg gct ctg gcc agc gga acc acc        537
Pro Ile Ile Gln Ala Ser Val Ala Arg Ala Leu Ala Ser Gly Thr Thr
        150                 155                 160 atg gac gcc gtg ctg gag atg ctg agg gag gtg acg ccg gag ctg tcg        585
Met Asp Ala Val Leu Glu Met Leu Arg Glu Val Thr Pro Glu Leu Ser
    165                 170                 175 tgc ccc gtg gtg ctc ctc tcc tac tac aag ccc atc atg tct cgc agc        633
Cys Pro Val Val Leu Leu Ser Tyr Tyr Lys Pro Ile Met Ser Arg Ser
180                 185                 190                 195 ttg gcc gag atg aaa gag gcg ggg gtc cac ggt ctt ata gtg cct gat        681
Leu Ala Glu Met Lys Glu Ala Gly Val His Gly Leu Ile Val Pro Asp
                200                 205                 210 ctc ccg tac gtg gcc gcg cac tcg ctg tgg agt gaa gcc aag aac aac        729
Leu Pro Tyr Val Ala Ala His Ser Leu Trp Ser Glu Ala Lys Asn Asn
            215                 220                 225 aac ctg gag ctg gtg ctg ctg aca aca cca gcc ata cca gaa gac agg        777
Asn Leu Glu Leu Val Leu Leu Thr Thr Pro Ala Ile Pro Glu Asp Arg
        230                 235                 240 atg aag gag atc acc aag gct tca gaa ggc ttc gtc tac ctg gtg agc        825
Met Lys Glu Ile Thr Lys Ala Ser Glu Gly Phe Val Tyr Leu Val Ser
    245                 250                 255 gtg aac gga gtg aca ggt cct cgc gca aac gtg aac cca cga gtg gag        873
Val Asn Gly Val Thr Gly Pro Arg Ala Asn Val Asn Pro Arg Val Glu
260                 265                 270                 275 tca ctc atc cag gag gtt aag aag gtg act aac aag ccc gtt gct gtt        921
Ser Leu Ile Gln Glu Val Lys Lys Val Thr Asn Lys Pro Val Ala Val
                280                 285                 290 ggc ttc ggc ata tcc aag ccc gag cac gtg aag cag att gcg cag tgg        969
Gly Phe Gly Ile Ser Lys Pro Glu His Val Lys Gln Ile Ala Gln Trp
            295                 300                 305 ggc gct gac ggg gtg atc atc ggc agc gcc atg gtg agg cag ctg ggc       1017
Gly Ala Asp Gly Val Ile Ile Gly Ser Ala Met Val Arg Gln Leu Gly
        310                 315                 320 gaa gcg gct tct ccc aag caa ggc ctg agg agg ctg gag gag tat gcc       1065
Glu Ala Ala Ser Pro Lys Gln Gly Leu Arg Arg Leu Glu Glu Tyr Ala
    325                 330                 335 agg ggc atg aag aac gcg ctg cca tgagtccatg acaaagtaaa acgtacagag       1119
Arg Gly Met Lys Asn Ala Leu Pro
340                 345 acacttgata atatctatct atcatctcgg agaagacgac cgaccaataa aaataagcca     1179
agtggaagtg aagcttagct gtatatacac cgtacgtcgt cgtcgtcgtt ccggatcgat     1239
ctcggccggc tagctagcag aacgtgtacg tagtagtatg taatgcatgg agtgtggagc     1299
tactagctag ctggccgttc attcgattat aattcttcgc tctgctgtgg tagcagatgt     1359
```

```
acctagtcga tcttgtacga cgaagaagct ggctagctag ccgtctcggt cgttaaaaaa    1419
aaaaaaaaaa aaaaaaaaaa aaaaaaaaaa aaaaaaaaaa aaaaaaaaaa aaaaaaaaaa    1479
aaaaaaaaaa aaaaaaaaaa aaggaattc                                      1508
```

<210> SEQ ID NO 2
<211> LENGTH: 347
<212> TYPE: PRT
<213> ORGANISM: Artificial Sequence
<220> FEATURE:
<223> OTHER INFORMATION: Description of Artificial Sequence: Synthetic

<400> SEQUENCE: 2

```
Met Ala Phe Ala Pro Lys Thr Ser Ser Ser Ser Leu Ser Ser Ala
  1               5                  10                  15

Leu Gln Ala Ala Gln Ser Pro Pro Leu Leu Arg Arg Met Ser Ser
                 20                  25                  30

Thr Ala Thr Pro Arg Arg Arg Tyr Asp Ala Ala Val Val Thr Thr
             35                  40                  45

Thr Thr Thr Ala Arg Ala Ala Ala Ala Val Thr Val Pro Ala Ala
         50                  55                  60

Pro Pro Gln Ala Pro Ala Pro Ala Pro Val Pro Pro Lys Gln Ala Ala
 65                  70                  75                  80

Ala Pro Ala Glu Arg Arg Ser Arg Pro Val Ser Asp Thr Met Ala Ala
                 85                  90                  95

Leu Met Ala Lys Gly Lys Thr Ala Phe Ile Pro Tyr Ile Thr Ala Gly
                100                 105                 110

Asp Pro Asp Leu Ala Thr Thr Ala Glu Ala Leu Arg Leu Leu Asp Gly
            115                 120                 125

Cys Gly Ala Asp Val Ile Glu Leu Gly Val Pro Cys Ser Asp Pro Tyr
        130                 135                 140

Ile Asp Gly Pro Ile Ile Gln Ala Ser Val Ala Arg Ala Leu Ala Ser
145                 150                 155                 160

Gly Thr Thr Met Asp Ala Val Leu Glu Met Leu Arg Glu Val Thr Pro
                165                 170                 175

Glu Leu Ser Cys Pro Val Val Leu Leu Ser Tyr Tyr Lys Pro Ile Met
            180                 185                 190

Ser Arg Ser Leu Ala Glu Met Lys Glu Ala Gly Val His Gly Leu Ile
        195                 200                 205

Val Pro Asp Leu Pro Tyr Val Ala Ala His Ser Leu Trp Ser Glu Ala
    210                 215                 220

Lys Asn Asn Asn Leu Glu Leu Val Leu Leu Thr Thr Pro Ala Ile Pro
225                 230                 235                 240

Glu Asp Arg Met Lys Glu Ile Thr Lys Ala Ser Glu Gly Phe Val Tyr
                245                 250                 255

Leu Val Ser Val Asn Gly Val Thr Gly Pro Arg Ala Asn Val Asn Pro
            260                 265                 270

Arg Val Glu Ser Leu Ile Gln Glu Val Lys Lys Val Thr Asn Lys Pro
        275                 280                 285

Val Ala Val Gly Phe Gly Ile Ser Lys Pro Glu His Val Lys Gln Ile
    290                 295                 300

Ala Gln Trp Gly Ala Asp Gly Val Ile Ile Gly Ser Ala Met Val Arg
305                 310                 315                 320

Gln Leu Gly Glu Ala Ala Ser Pro Lys Gln Gly Leu Arg Arg Leu Glu
                325                 330                 335
```

Glu Tyr Ala Arg Gly Met Lys Asn Ala Leu Pro
        340                 345

<210> SEQ ID NO 3
<211> LENGTH: 2182
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3

| | | | | | |
|---|---|---|---|---|---|
| ccccgtacta | gagaaatatg | ccctccgcga | tcaagtctma | tcgacctcct | mcgggtgtct | 60 |
| tcgtccccgg | cgacagtcca | ctcgtccccg | ttatcgaagc | gcctaccagc | tgcagtggcc | 120 |
| atgccggggc | ggcggaggtc | tgtggccact | gtaagggcgg | tcgccgcggt | agctccggct | 180 |
| gccccggcgg | cgccggccaa | gctcaccgcc | ggtgccggcg | ggcgatgcct | gcggtgtcgc | 240 |
| aggaccattt | ccaggtcagg | ggcagcggaa | rgtattyaca | trcgtggttc | ttccgcgatg | 300 |
| ctgccggttt | cgcagacatg | tcgtctgcat | ctgcactctc | cagtactatt | atgtaggcac | 360 |
| agccatgtac | gggtcctgac | ttggaactcc | gttgtgacgt | cgtggttctc | gcagacggcg | 420 |
| ttcatcccgt | acatcaccgc | cgccgacccg | gacctgccga | cgacgacgga | ggaggcgctg | 480 |
| cggctcctgg | acgcctgcgg | cgccgacgtc | atcgagctcg | gcgttccctt | ctcggacccc | 540 |
| tacgccgacg | ggccggtcat | ccaggcgtcg | gcggcgcggg | cactggcgag | cggcacgacg | 600 |
| ccggacggcg | tgctggcgat | gctgaaggag | gtgacgccgg | agctgtcctg | ccccgtggtg | 660 |
| ctcttctcct | acttcaaccc | catcgtgcgg | tggggcctgg | ccgacttcgc | cgccgccgtc | 720 |
| aaggaagccg | gcgtgcacgg | cctcatagtt | cccgacctcc | cgtatgggaa | ctcgtgtgct | 780 |
| ctcactctca | ggaccgaagc | catcaagaac | agcctcgagc | tggtatgtaa | tatcaaggag | 840 |
| aagcacgtgc | gtcgtctcct | agttcttctg | cgcaatataa | aattgagaaa | gcagcgtctg | 900 |
| tctcacgaca | tgaacaatgg | ctgaacacat | gcagtgctgc | tcacaacacc | atcctacgcc | 960 |
| agcggacagg | atggaggaga | taacacgagc | ttccgaggat | tcgtctatct | cgtaagtgcc | 1020 |
| caaaactttc | cgtccaggag | ttttgctagc | gactgaactt | gccggccgat | gacatgcatg | 1080 |
| catgctcatc | tatcctactt | gaccatcaca | cgcgaccgtc | aatggagtta | caggtccacg | 1140 |
| cgcaaacgtg | aacacacgtg | tccagtctct | cattcaggag | gttaaacagg | taataatacg | 1200 |
| tcttgccaaa | ggaaaaggag | agaaaagaga | gcgagagaga | aaagatgcc | atttttattc | 1260 |
| gttttttgttg | ttaccaatca | caatcactga | gctggctggc | ttgtgttttt | ttgtttgctg | 1320 |
| caggtcactg | acatacccgt | ggctgtcggg | tttggcatat | cgaaacctga | gcatgtaaag | 1380 |
| caggtaggca | aaactttttt | aaaaaaaatg | cctcaaaaac | ttattcacat | attttttttat | 1440 |
| agtaacaaat | tctaacagta | tatatattgc | acctggacag | attgcagagt | ggggtgcaga | 1500 |
| tggtgtgatc | attggtagcg | caatggtgag | acagttaggc | gaagcagcct | ctcccaagga | 1560 |
| aggattgaag | aggctagaga | aatacgccag | gagcatgaag | aacgcgctac | catgccagtg | 1620 |
| aactagtcgt | tatgacgcga | tataggctgt | gttagcaagc | acgttgggag | aacaatgttg | 1680 |
| cagaagtagc | acamttaata | atgatccatt | cggcaaggtt | gcttttttac | aaattgcaac | 1740 |
| aataagttat | caatattaaa | tcaacgattc | cttgtttaaa | aaaaggaag | aaatgttaca | 1800 |
| tcattggatg | gtgctgcgat | tcagtggtta | ctccattcat | tttaaattac | agttcagctc | 1860 |
| gagtttggcc | tgactcagcc | tttttaaaga | ttgtcaattt | gtgacaacaa | caacaataat | 1920 |

-continued

| | |
|---|---|
| aataataagt gggtagctca ttacattctw caaaaatctt gatatgcatt tatctgaact | 1980 |
| tgtggggatg ttatcataac tttctagcaa ttctcaaatt agtagggaag gtttggaatc | 2040 |
| acaggttaaa gaactwaaag tgagctacat ttcaaaacat mcggagggga atatcaatgt | 2100 |
| gtgtacacca ctatagaacg cggcccatca gttccaatta aatttaggct agagaccaat | 2160 |
| gtgatcatca gttttgattc ta | 2182 |

<210> SEQ ID NO 4
<211> LENGTH: 2159
<212> TYPE: DNA
<213> ORGANISM: Artificial Sequence
<220> FEATURE:
<223> OTHER INFORMATION: Description of Artificial Sequence: Synthetic Primer

<400> SEQUENCE: 4

| | |
|---|---|
| aggaggaacg aacggacagg ttgttgcaca gaagcgacat ggctttcgcg cccaaaacgt | 60 |
| cctcctcctc ctcgctgtcc tcggcgttgc aggcagctca gtcgccgccg ctgctcctga | 120 |
| ggcggatgtc gtcgaccgca acaccgagac ggaggtacga cgcggccgtc gtcgtcacta | 180 |
| ccaccaccac tgctagagct gcggcggctg ctgtcacggt tcccgccgcc ccgccgcagg | 240 |
| cgggccgccg ccgccggtgc caccaaagca agcggcggca cccgcagagg aggagccgtc | 300 |
| cggtgtcgga caccatggcg gcgctcatgg ccaagggcaa ggttcgtata gtacgcgcgc | 360 |
| gtgtcgtcgt cgttattttg cgcataggcg cggacataca cgtgctttag ctagctaaca | 420 |
| gctagatcat cggtgcagac ggcgttcatc ccgtacatca ccgccggcga cccggaccta | 480 |
| gcgacgacgg ccgaggcgct cgtctgctg acggctgtg gcgccgacgt catcgagctg | 540 |
| ggggtacct gctcggaccc ctacatcgac gggcccatca tccaggcgtc ggtggcgcgg | 600 |
| gctctggcca gcggcaccac catggacgcc gtgctggaga tgctgaggga ggtgacgccg | 660 |
| gagctgtcgt gccccgtggt gctcctctcc tactacaagc ccatcatgtc tcgcagcttg | 720 |
| gccgagatga aagaggcggg ggtccacggt aactatagct agctcttccg atcccccttc | 780 |
| aattaattaa tttatagtag tccattcatg tgatgatttt tgttttcttt tttactgaca | 840 |
| ggtcttatag tgcctgatct cccgtacgtg gccgcgcact cgctgtggag tgaagccaag | 900 |
| aacaacaacc tggagctggt aggttgaatt aagttgatgc atgtgatgat ttatgtagct | 960 |
| agatcgagct agctataatt aggagcatat caggtgctgc tgacaacacc agccatacca | 1020 |
| gaagacagga tgaaggagat caccaaggct tcagaaggct tcgtctacct ggtagttata | 1080 |
| tgtatatata gatggacgac gtaactcatt ccagccccat gcatatatgg aggcttcaat | 1140 |
| tctgcagaga cgacgaagac cacgacgacg actaacacta gctaggggcg tacgttgcag | 1200 |
| gtgagcgtga acggagtgac aggtcctcgc gcaaacgtga acccacgagt ggagtcactc | 1260 |
| atccaggagg ttaagaaggt gactaacaag cccgttgctg ttggcttcgg catatccaag | 1320 |
| cccgagcacg tgaagcaggt acgtacgtag ctgaccaaaa aaaactgtta acaagttttg | 1380 |
| tttgacaagc cggctactag ctagctaaca gtgatcagtg acacacacac acacacagat | 1440 |
| tgcgcagtgg ggcgctgacg gggtgatcat cggcagcgcc atggtgaggc agctgggcga | 1500 |
| agcggcttct cccaagcaag gcctgaggag gctggaggag tatgccaggg gcatgaagaa | 1560 |
| cgcgctgcca tgagtccatg acaaagtaaa acgtacagag acacttgata atatctatct | 1620 |
| atcatctcgg agaagacgac cgaccaataa aaataagcca agtggaagtg aagcttagct | 1680 |
| gtatatacac cgtacgtcgt cgtcgtcgtt ccggatcgat ctcggccggc tagctagcag | 1740 |

-continued

```
aacgtgtacg tagtagtatg taatgcatgg agtgtggagc tactagctag ctggccgttc   1800
attcgattat aattcttcgc tctgctgtgg tagcagatgt acctagtcga tcttgtacga   1860
cgaagaagct ggctagctag ccgtctcgat cgtatatgta ctgattaatc tgcagattga   1920
ataaaaacta cagtacgcat atgatgcgta cgtacgtgtg tatagtttgt gctcatatat   1980
gctcctcatc acctgcctga tctgcccatc gatctctctc gtactccttc ctgttaaatg   2040
ccttctttga cagacacacc accaccagca gcagtgacgc tctgcacgcc gccgctttaa   2100
gacatgtaag atattttaag aggtataaga taccaaggag cacaaatctg gagcactgg   2159
```